(12) United States Patent
Gosik-Wolfe et al.

(10) Patent No.: US 11,399,961 B2
(45) Date of Patent: Aug. 2, 2022

(54) IMPLANT EXTRACTOR TOOL

(71) Applicant: Shukla Medical, St. Petersburg, FL (US)

(72) Inventors: Adam Gosik-Wolfe, Tampa, FL (US); Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 92 days.

(21) Appl. No.: 16/743,085

(22) Filed: Jan. 15, 2020

(65) Prior Publication Data

US 2020/0222205 A1 Jul. 16, 2020

Related U.S. Application Data

(60) Provisional application No. 62/792,467, filed on Jan. 15, 2019.

(51) Int. Cl.
*A61F 2/46* (2006.01)
*A61B 17/02* (2006.01)

(52) U.S. Cl.
CPC ............ *A61F 2/4603* (2013.01); *A61F 2/46* (2013.01); *A61B 17/025* (2013.01); *A61F 2002/4619* (2013.01); *A61F 2002/4628* (2013.01)

(58) Field of Classification Search
CPC .............. A61F 2/4612; A61F 2/4603; A61F 2002/4619; A61F 2002/4622; A61F 2002/4625; A61F 2002/4627; A61F 2002/4628; A61F 2002/4641; A61B 17/025
See application file for complete search history.

(56) References Cited

U.S. PATENT DOCUMENTS

| | | | |
|---|---|---|---|
| 2005/0010213 A1* | 1/2005 | Stad | A61B 17/025 606/53 |
| 2017/0056070 A1* | 3/2017 | Buss | A61F 2/4611 |
| 2017/0281365 A1* | 10/2017 | Robinson | A61F 2/4611 |
| 2018/0104070 A1* | 4/2018 | VanDiepenbos | A61F 2/461 |

* cited by examiner

*Primary Examiner* — Amy R Sipp
(74) *Attorney, Agent, or Firm* — Kim IP Law Group LLC

(57) ABSTRACT

An implant extractor tool including first and second pivotably connected arms having jaws at their distal ends adapted to engage an implant. The tool further includes an adjustment mechanism having an adjuster and a biasing member biasing one of the first and second arms, and an actuator operatively engageable with the adjustment mechanism. The actuator is movable between a first position locking the adjustment mechanism in a fixed position and a second position spaced from the adjustment mechanism permitting movement of the adjustment mechanism relative to the actuator. The implant extraction tool can be operated using one hand to engage an implant to be extracted.

23 Claims, 32 Drawing Sheets

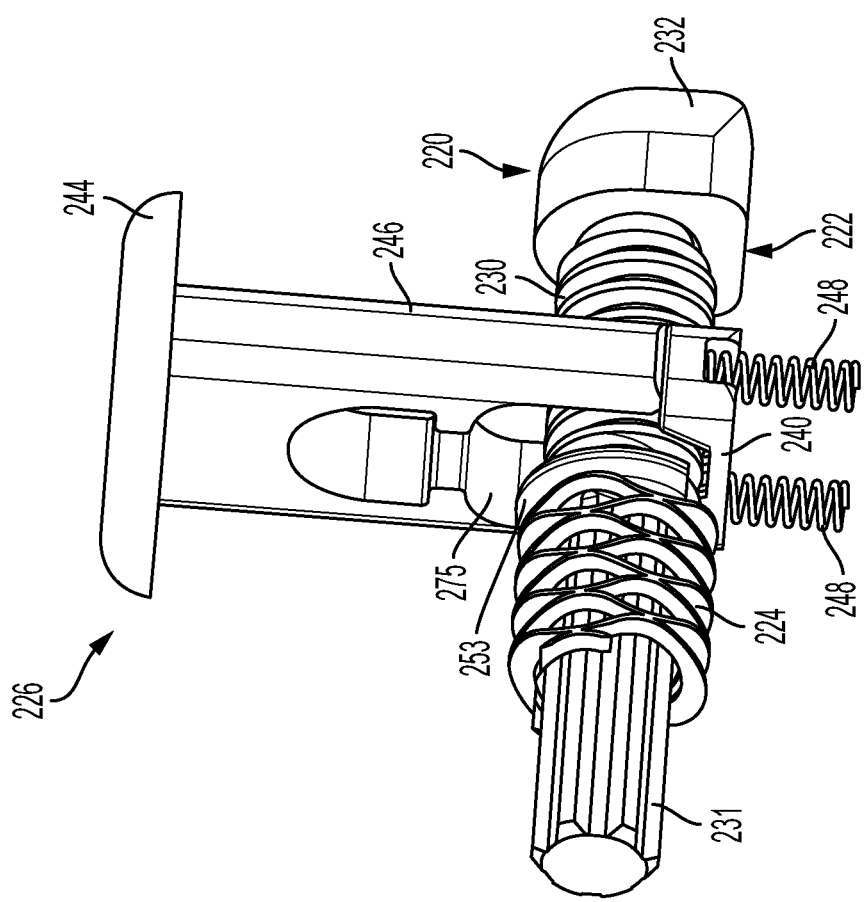

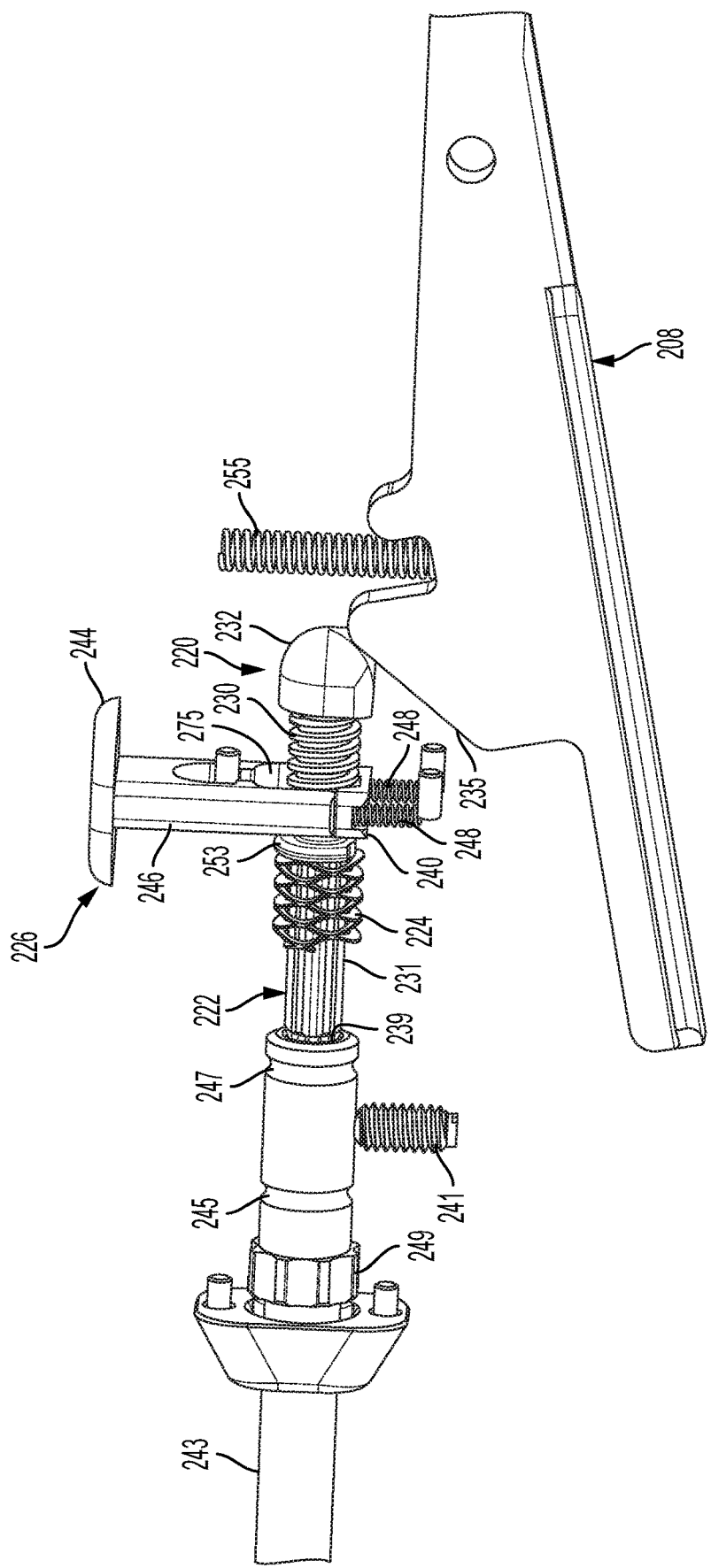

IMPLANT EXTRACTOR TOOL

CROSS-REFERENCE TO RELATED APPLICATION

This application claims the benefit under 35 U.S.C. § 119(e) to U.S. Provisional Application No. 62/792,467, filed Jan. 15, 2019, and entitled "Extractor Tool," the entire disclosure of which is hereby incorporated by reference for all purposes.

BACKGROUND OF THE DISCLOSURE

The exemplary embodiments of present invention relate generally to a surgical extraction tool and, more specifically, to a tool for extracting an implant including, without limitation, a glenosphere implant, from bone.

Typical implant extractor tools, including those used to extract a glenosphere from bone, require a user (e.g., a surgeon) to use two hands to manipulate the tool to engage an implant to be extracted. More specifically, a user must hold the tool with one hand while turning an adjuster with the other hand until the jaws of the tool engage the implant. Such a procedure occupies both of the user's hands and requires considerable manual dexterity to align and hold the tool in the proper position with respect to the implant while turning the adjuster.

BRIEF SUMMARY OF THE DISCLOSURE

In accordance with an exemplary embodiment there is provided an implant extractor tool comprising a first arm having a proximal end for attachment to an extraction device, and a distal end opposite the proximal end. The tool further comprises a second arm pivotably connected to the first arm, the second arm having a proximal end and a distal end. The tool further includes a first jaw releasably attachable to the distal end of the first arm, and a second jaw releasably attachable to the distal end of the second arm. The tool additionally comprises an adjustment mechanism operatively connected to one of the first and second arms for engaging the other of the first and second arms. The adjustment mechanism includes an adjuster, and a biasing member biasing one of the first and second arms. The tool further comprises an actuator operatively engageable with the adjustment mechanism. The actuator is movable between a first position locking the adjustment mechanism in a fixed position and a second position spaced from the adjustment mechanism permitting movement of the adjustment mechanism relative to the actuator.

According to an aspect, the adjuster includes a threaded shaft and a control knob. According to another aspect, the adjuster further comprises a domed distal end. According to another aspect, the biasing member surrounds the adjuster. According to another aspect, the actuator comprises a latch moveable between a locking position for locking the adjustment mechanism in the fixed position and an unlocking position spaced from the adjustment mechanism. According to another aspect, the latch is completely housed within one of the first and second arms. According to another aspect, the actuator further comprises a knob or actuation button, a shaft extending from the knob or actuation button, a latch about a distal end of the shaft, and an actuator biasing member biasing the latch. According to another aspect, the adjuster is received within a through hole of one of the first and second arms.

According to another aspect, the implant extractor tool further comprises an attachment mechanism configured to releasably attach an extraction device to a proximal end of one of the first and second arms. According to another aspect, the attachment mechanism comprises a retaining housing having a central cavity for receiving a handle extension of an extraction device, and a locking mechanism moveable between first and second positions relative to the retaining housing, the locking mechanism having a through hole for receiving the handle extension. According to another aspect, the attachment mechanism further comprises a biasing member that biases the locking mechanism towards the first position. According to another aspect, the locking mechanism defines a lip that partially occludes the central cavity from receiving the handle extension. According to another aspect, at least one of the first and second arms comprises a latch for releasably retaining a respective first jaw or second jaw.

According to another aspect, the adjuster includes a splined shaft and a bulbous end. According to another aspect, the biasing member surrounds the splined shaft. According to another aspect, the adjuster extends through a through hole of the actuator. According to another aspect, the adjuster is housed completely within one of the first and second arms. According to another aspect, the implant extractor tool further comprises an arms biasing member biasing the first and second arms. According to another aspect, one of the first and second arms includes a cam surface engaged with the adjuster.

According to another aspect, one of the first and second arms includes an attachment mechanism comprising a fastener for releasably attaching an extraction device or handle to its proximal end. According to another aspect, the implant extractor tool further comprises a handle attached to a proximal end of the first arm, and wherein the adjustment mechanism and actuator is mounted to the first arm.

In accordance with the exemplary embodiments of the subject disclosure, there is provided an implant extraction tool that can be operated using one hand to engage the extraction tool to an implant to be extracted. Other features and advantages of the subject disclosure will be apparent from the following more detailed description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

FIG. 22 is a perspective view of an adjustment mechanism and actuator of the implant extraction tool of FIG. 18;

FIG. 25 is a side view of the implant extraction tool of FIG. 18 with certain elements omitted for purposes of clarity.

DETAILED DESCRIPTION OF THE DISCLOSURE

Figure 1:
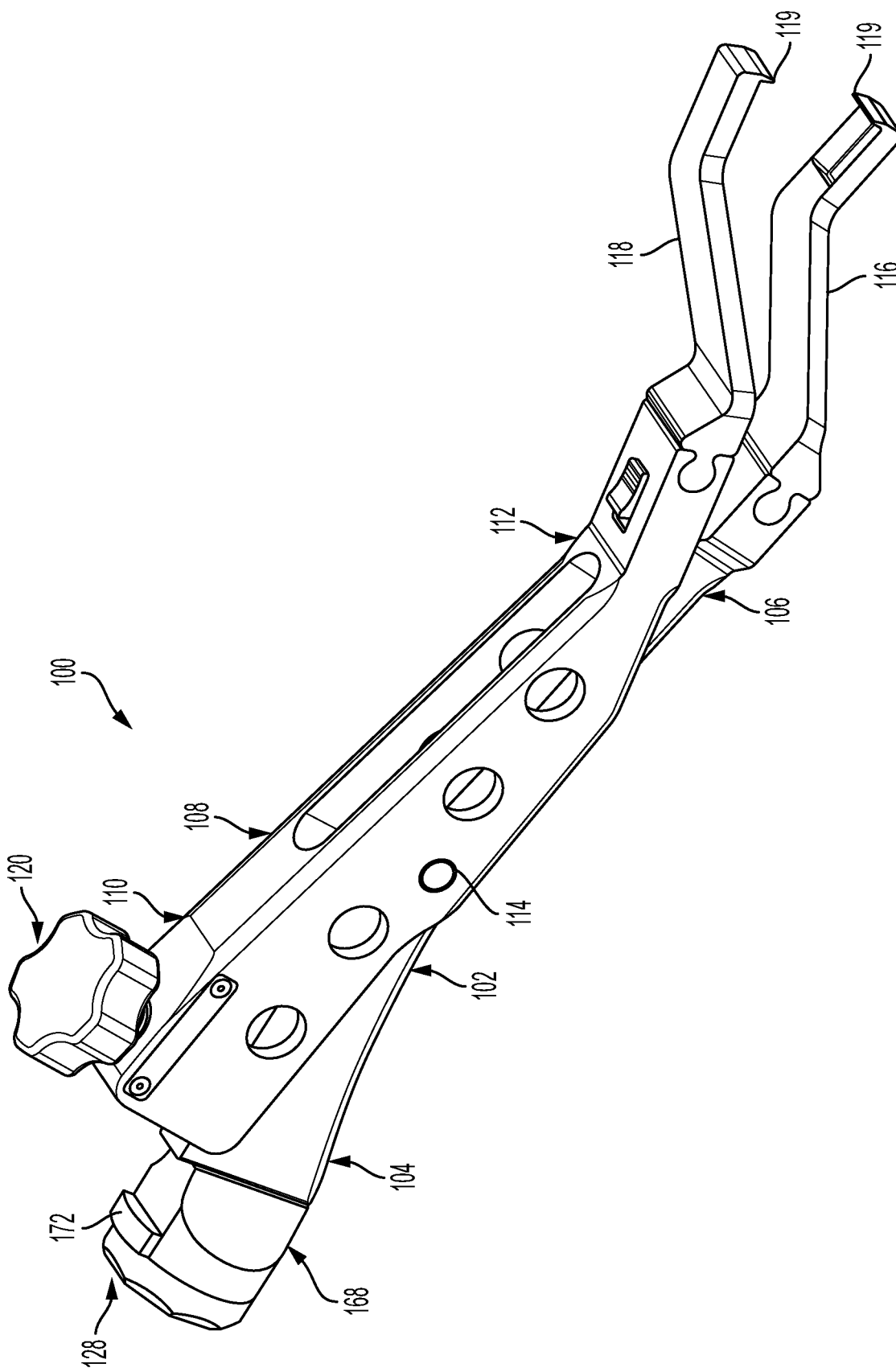
FIG. 1 is perspective view of an implant extraction tool in accordance with an exemplary embodiment of the subject disclosure.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Referring now to the drawings, FIGS. 1 through 17 illustrate an implant extractor tool 100 in accordance with an exemplary embodiment of the present disclosure. The extractor tool 100 includes a first arm 102, a second arm 108, an adjustment mechanism 120 operatively connected to one of the first and second arms for engaging the other of the first and second arms, and an actuator 126. The first arm includes a proximal end 104 for attachment to an extraction device and a distal end 106 opposite the proximal end. The second arm 108 is pivotably connected to the first arm and includes a proximal end 110 and a distal end 112. The adjustment mechanism 120 includes an adjuster 122 and a biasing member 124 biasing one of the first and second arms. The actuator 126 is operatively engageable with the adjustment mechanism and movable between a first position locking the adjustment mechanism in a fixed position and a second position spaced from the adjustment mechanism permitting movement of the adjustment mechanism relative to the actuator.

Figure 4A:
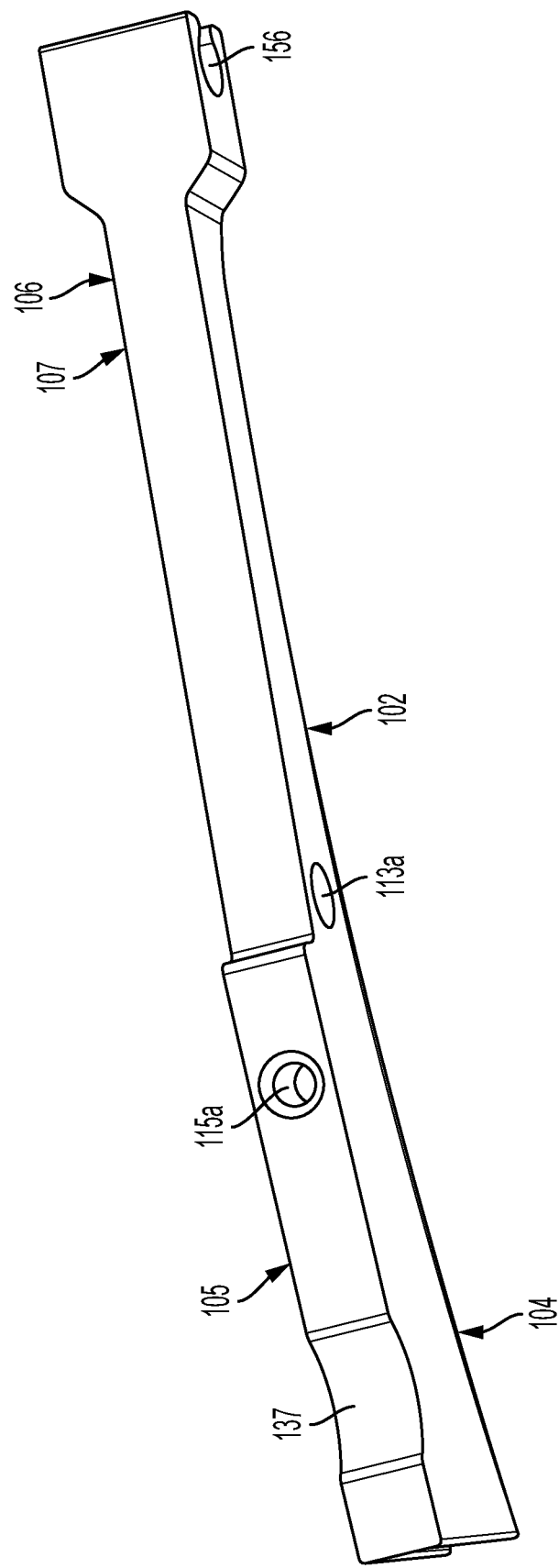
FIG. 4A is a top perspective view of a first arm of the implant extraction tool of FIG. 1.
Figure 4B:
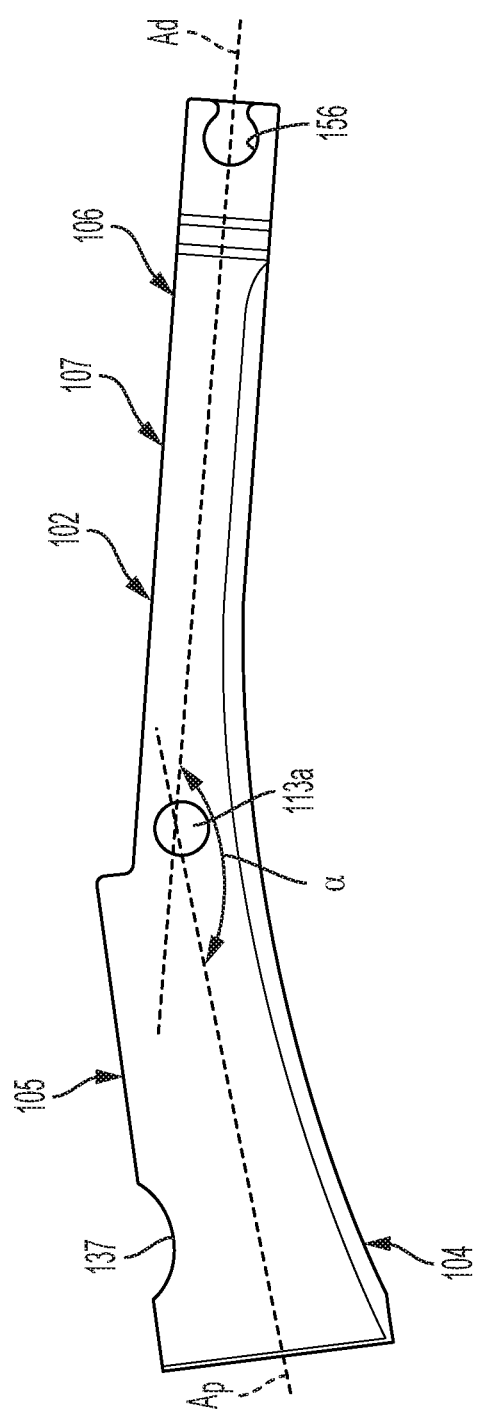
FIG. 4B is a side view of the first arm of the implant extraction tool of FIG. 1.

The first arm 102 is configured as best shown in FIGS. 4A and 4B in accordance with an exemplary construction of the present disclosure. The first arm 102 is an elongated arm which can be of unitary construction having the proximal end 104 configured to receive the extraction device attachment mechanism 128.

The first arm includes a proximal arm segment 105 and a distal arm segment 107 having a longitudinal axis "$A_d$" at an angle α of about 90 to 180 degrees, and preferably about 160 to 170 degrees, including 100, 110, 120, 130, 140, 150, 165, and 175 degrees relative to a longitudinal axis "$A_p$" of the proximal arm segment. The angled configuration of the proximal and distal arm segments provide for greater expansion between the distal ends of the first and second arms. The proximal arm segment is generally trapezoidal in shape having a taper or tapering in the distal direction from its most proximal end.

Figure 3:
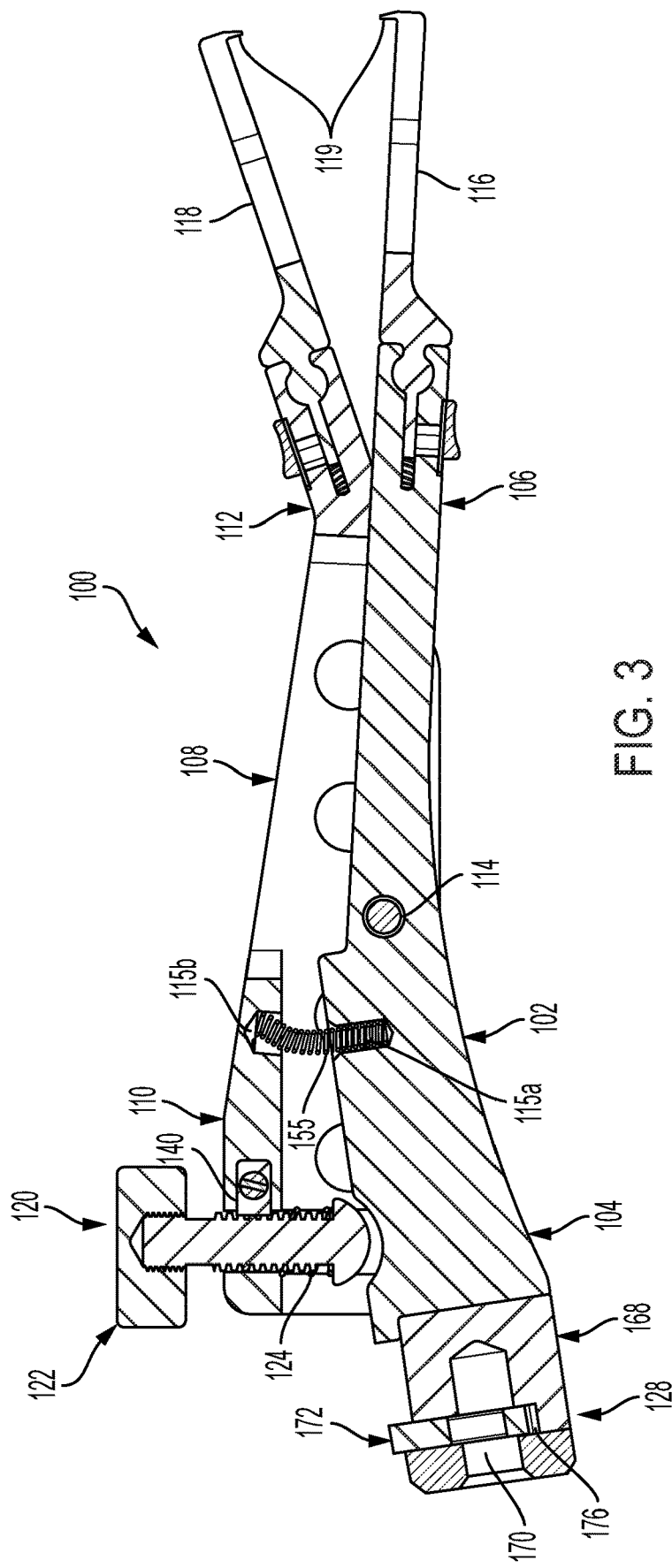
FIG. 3 is a cross-sectional view of the implant extraction tool of FIG. 2.

FIG. 4A shows an anterior face of the first arm, which includes a counterbore 115a for receiving a biasing member 155 (as shown in FIG. 3) for biasing the first and second arms 102, 108 toward the open or retracted position. The counterbore 115a is positioned about a midportion of the first arm, and preferably about a midportion of the first arm on the proximal arm segment 105. The first arm also includes a recess 137 e.g., a concavity or scallop, facing anteriorly about a proximal end of the first arm for engaging a distal end 136 of the adjuster 122, as further discussed below.

FIG. 4B illustrates a lateral side of the first arm. The first arm further includes a recess 113a e.g., a through hole, for receiving a pivot e.g., a pivot pin 114 (FIGS. 1 and 2), about which the first arm pivots relative to the second arm. The recess is positioned on the first arm having a central axis or rotational axis substantially perpendicular or transverse to the longitudinal axis of the proximal or distal arm segments.

In accordance with another aspect of the exemplary embodiment, the first arm can include a receptacle 156 about its distal end for receiving and/or attaching to a first jaw, as described below. The receptacle 156 is preferably configured as a female housing having a laterally facing opening e.g., the receptacle on the first arm faces laterally, in a direction substantially perpendicular or transverse to the direction the recess 137 faces.

Figure 5A:
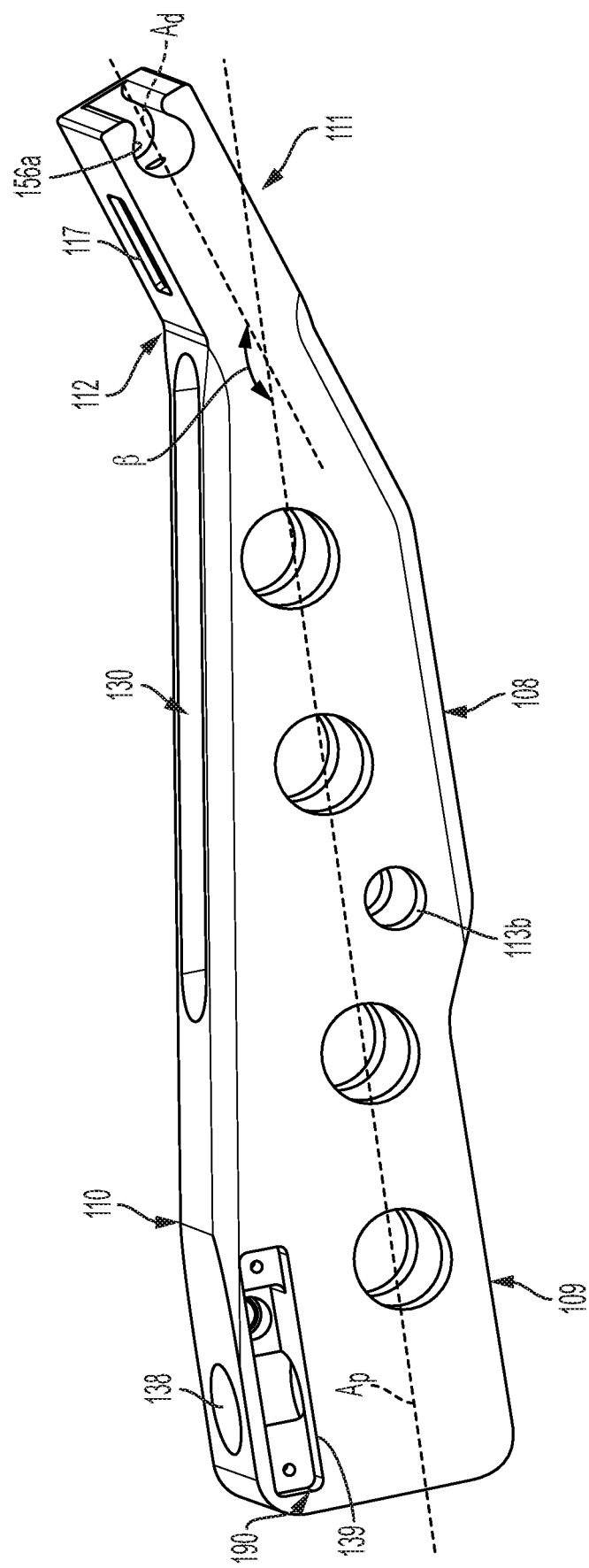
FIG. 5A is a top perspective view of a second arm of the implant extraction tool of FIG. 1.
Figure 5B:
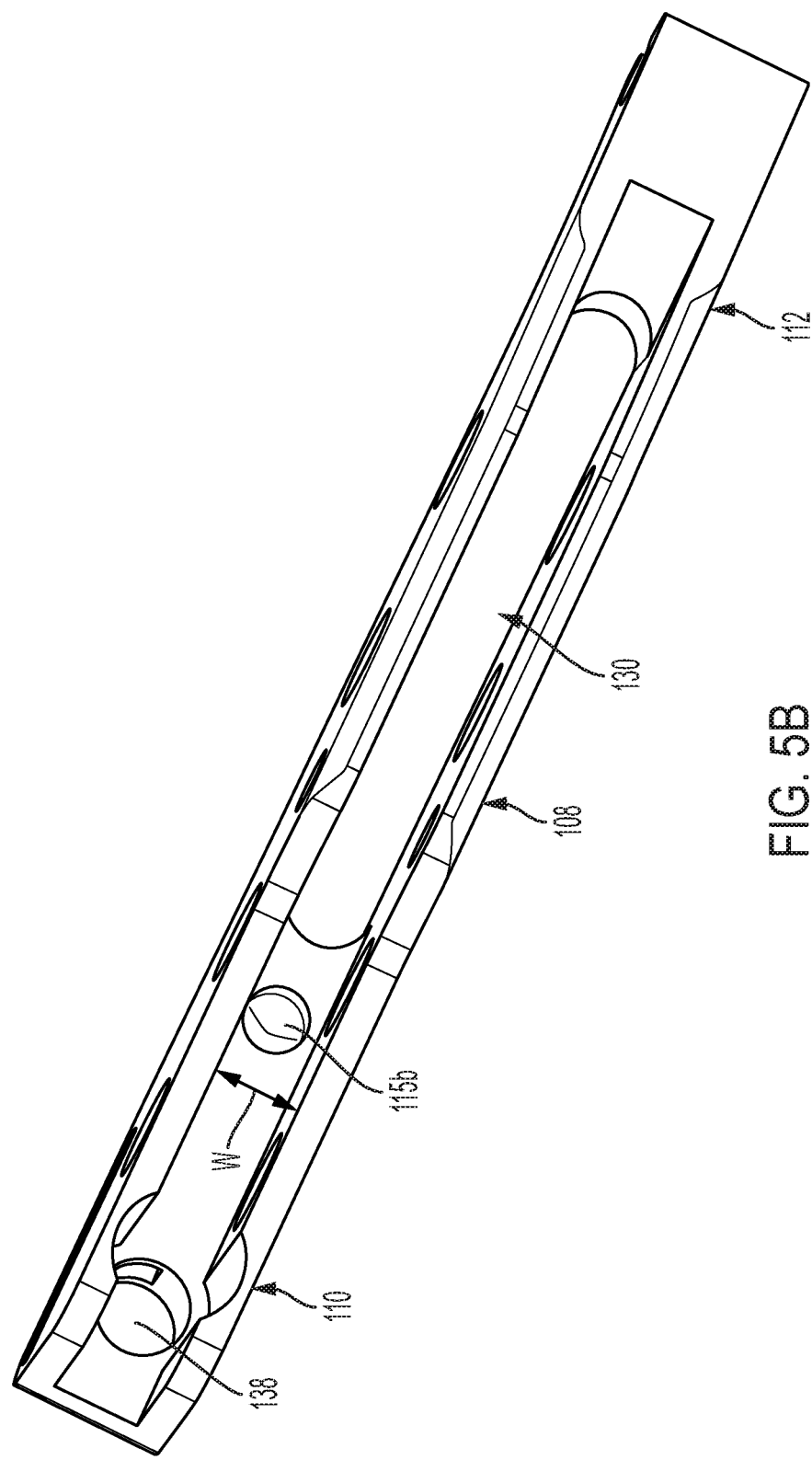
FIG. 5B is a bottom perspective view of the second arm of the implant extraction tool of FIG. 1.
Figure 5C:
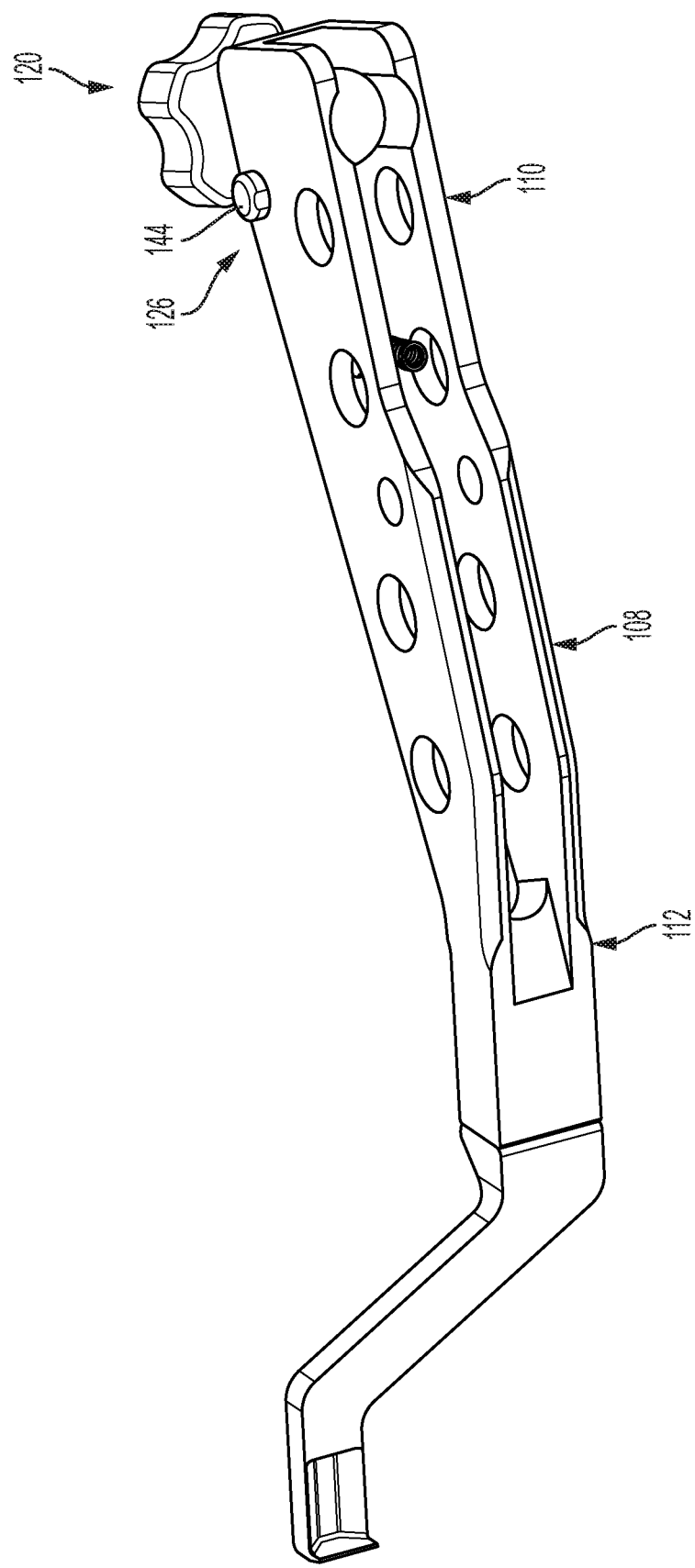
FIG. 5C is another bottom perspective view of the second arm of the implant extraction tool of FIG. 1.

FIGS. 5A through 5C best illustrate an exemplary construction of the second arm 108. In addition to the proximal end 110 and the distal end 112, the second arm has a generally open central region 130 configured to receive the first arm 102. That is, the open central region is, e.g., an opening or through hole that faces in the anterior direction of the second arm. The opening is an elongated opening that substantially spans the length of the midportion of the second arm. The second arm is configured to have an anterior facing side with depending lateral sides so as to form a substantially hollow U-shaped frame. The lateral sides are spaced apart a width "W" sufficient to receive the first arm therein.

Additionally, the second arm 108 is an elongated arm having a proximal arm segment 109 and a distal arm segment 111 having a longitudinal axis "$A_d$" at an angle β of about 90 to 180 degrees, and preferably about 150 to 170 degrees, including 100, 110, 120, 130, 140, 160, and 175 degrees relative to a longitudinal axis "$A_p$" of the proximal arm segment. The second arm further includes a through hole 113b about its midportion having a longitudinal axis substantially perpendicular or transverse to the longitudinal axis of the second arm. That is, the through hole 113b faces a lateral side of the second arm and is alignable with the through hole 113a of the first arm to receive the pivot pin 114.

The second arm also includes a recess 115b (FIG. 5B) for receiving a second end of the biasing member 155 that biases the first and second arms 102, 108. The recess, e.g., a counterbore, is a posteriorly facing recess and is positioned adjacent the opening 130. The second arm further includes an anteriorly facing through hole 138 (FIGS. 5A and 5B) in the proximal arm segment 109 for receiving the adjuster 122, as further described below. In addition, the second arm includes a housing 190 having a laterally facing opening 139 (FIG. 5A) in the proximal arm segment 109 for receiving the actuator 126, as further described below.

The second arm can additionally include a receptacle 156a about its distal end. The receptacle 156a is preferably configured as a female housing having a laterally facing opening for receiving and/or attaching to a second jaw. Furthermore, the second arm can include an anteriorly facing opening 117 in the distal end segment 111 for receiving a latch 150 (FIG. 11) that releasably retains the second jaw in the receptacle 156a.

The adjustment mechanism 120 is configured as best shown in FIGS. 3 and 6-8. The adjustment mechanism is operatively connected to one of the first and second arms for engaging the other of the first and second arms (in the illustrated example the adjustment mechanism 120 is connected to the second arm 108). The adjustment mechanism includes the adjuster 122 and the biasing member 124.

Figure 6:
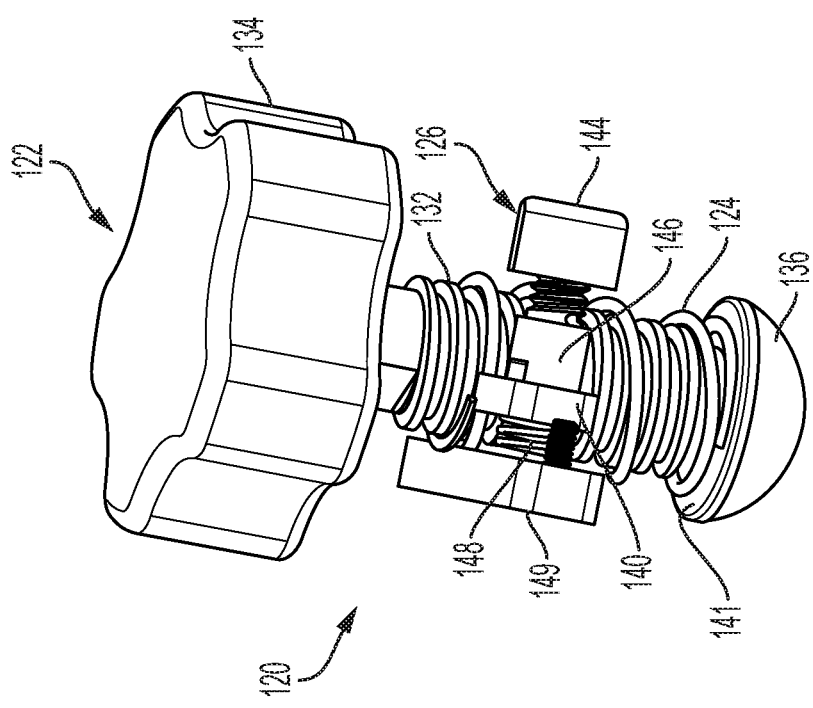
FIG. 6 is a perspective view of an adjustment mechanism and actuator of the implant extraction tool of FIG. 1.
Figure 7:
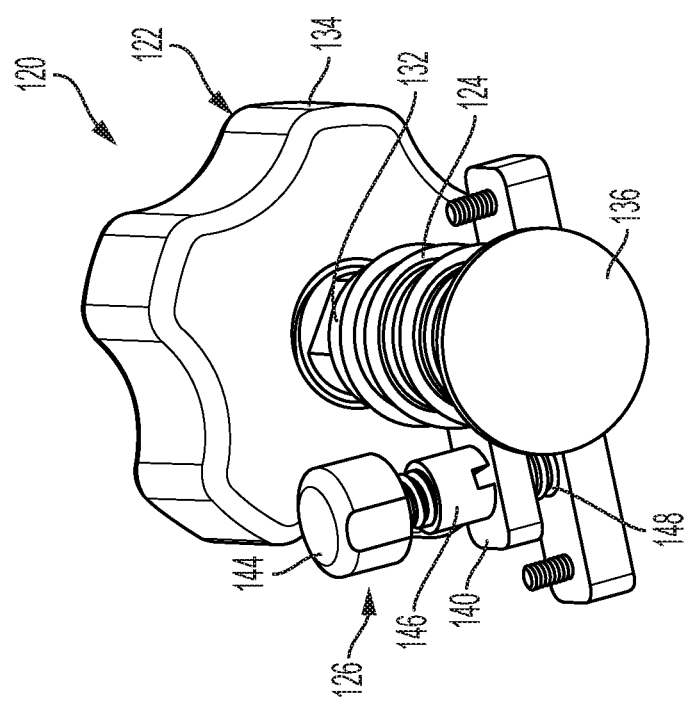
FIG. 7 is a bottom perspective view of the adjustment mechanism and actuator of FIG. 6.
Figure 8:
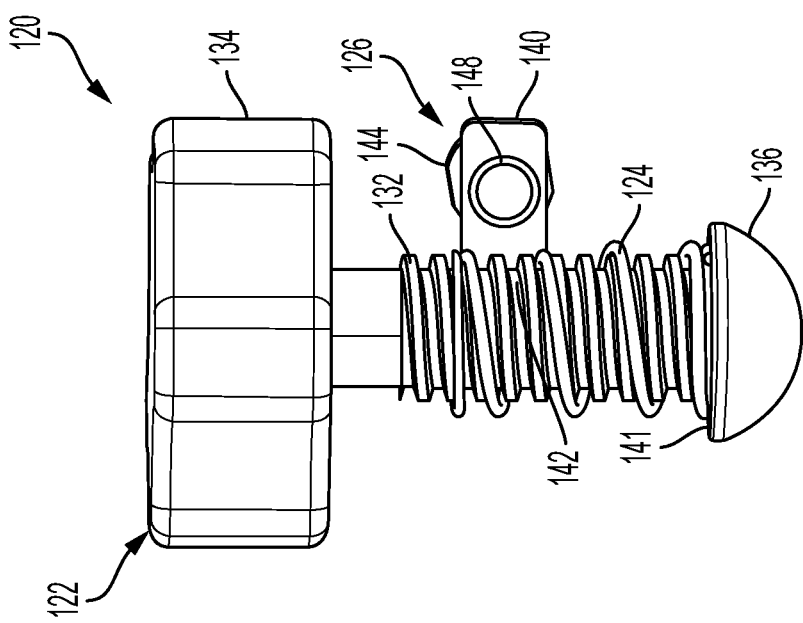
FIG. 8 is a side view of the adjustment mechanism and actuator of FIG. 6.

FIGS. 6 through 8 best illustrate an exemplary construction of the adjuster 122. The adjuster comprises a shaft e.g., a threaded shaft 132, and a control knob 134 at a proximal end of the shaft. The adjuster additionally comprises a domed distal end 136 about a distal end of the shaft 132 adapted for contacting the concave or scalloped recess 137 provided in the proximal end of the first arm 102 (FIGS. 4A and 4B). The domed distal end has an overall width greater than the overall diameter of the shaft so as to form a flange-like surface 141 (FIGS. 6 and 8). The adjuster 122 is received within the through hole 138 of the second arm 108 (FIGS. 5A and 5B). The through hole 138 is sized to receive the shaft 132 therein, but is smaller than an overall diameter of the domed distal end.

The biasing member 124 surrounds the adjuster 122, in particular the threaded shaft 132 and extends substantially the entire length of the shaft. The biasing member can be, e.g., a spring or an annular elastomer. In the illustrated embodiment, the biasing member is a compression spring.

FIGS. 6 through 9 best illustrate an exemplary construction of the actuator 126. The actuator 126 is operatively engageable with the adjustment mechanism 120. As will be described in greater detail below, the actuator 126 is movable between a first position locking the adjustment mechanism in a fixed position and a second position spaced from the adjustment mechanism permitting movement of the adjustment mechanism relative to the actuator. The actuator 126 comprises a knob 144, a threaded shaft 146 having a cylindrical-like end, a latch 140, and an actuator biasing member 148. According to an aspect, the actuator comprises the latch 140 moveable between a locking position for locking the adjustment mechanism in the fixed position and an unlocking position spaced from the adjustment mechanism. The latch 140 is completely housed within one of the first and second arms (in the illustrated example of FIG. 5C, the latch is completely housed within the second arm 108 in housing 190).

Figure 9:
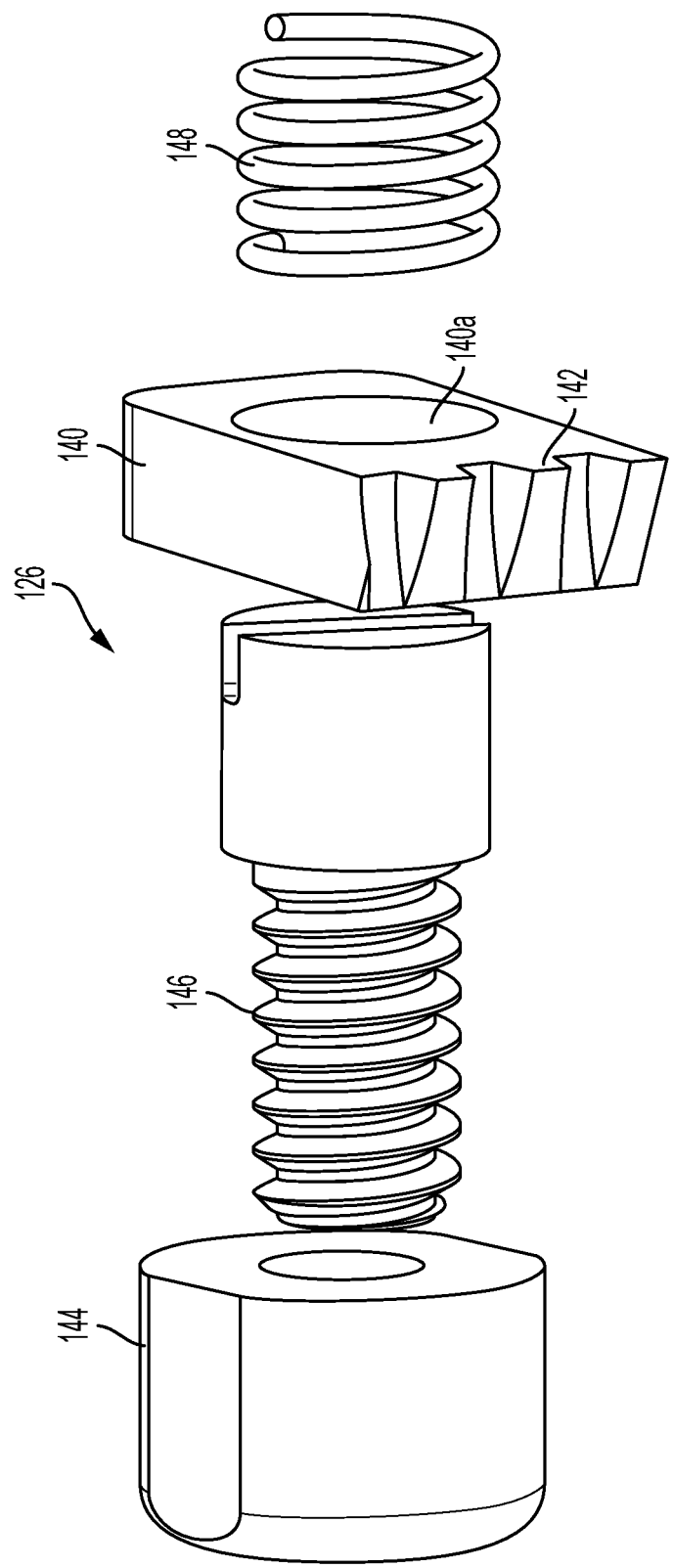
FIG. 9 is an enlarged exploded view of the actuator of the implant extraction tool of FIG. 1.

The latch 140 is configured as best shown in FIG. 9 and includes a substantially rectangular body having a through hole 140a for receiving the shaft 146, e.g. a threaded shaft. The latch 140 is provided with teeth or splines 142 that releasably engage the threads of the threaded shaft 132 of the adjuster 122 and configured to matingly engage the threads of the threaded shaft. The latch is disposed about a distal end of the shaft 146 such that the teeth or splines 142 face a lateral direction of the body. That is, the teeth 142 face substantially transverse to a longitudinal axis of the shaft 146.

The actuator biasing member 148 is positioned between the latch and a cover 149 that is rigidly connected to the second arm. The actuator biasing member may be, e.g., a spring or an elastomer.

Figure 2:
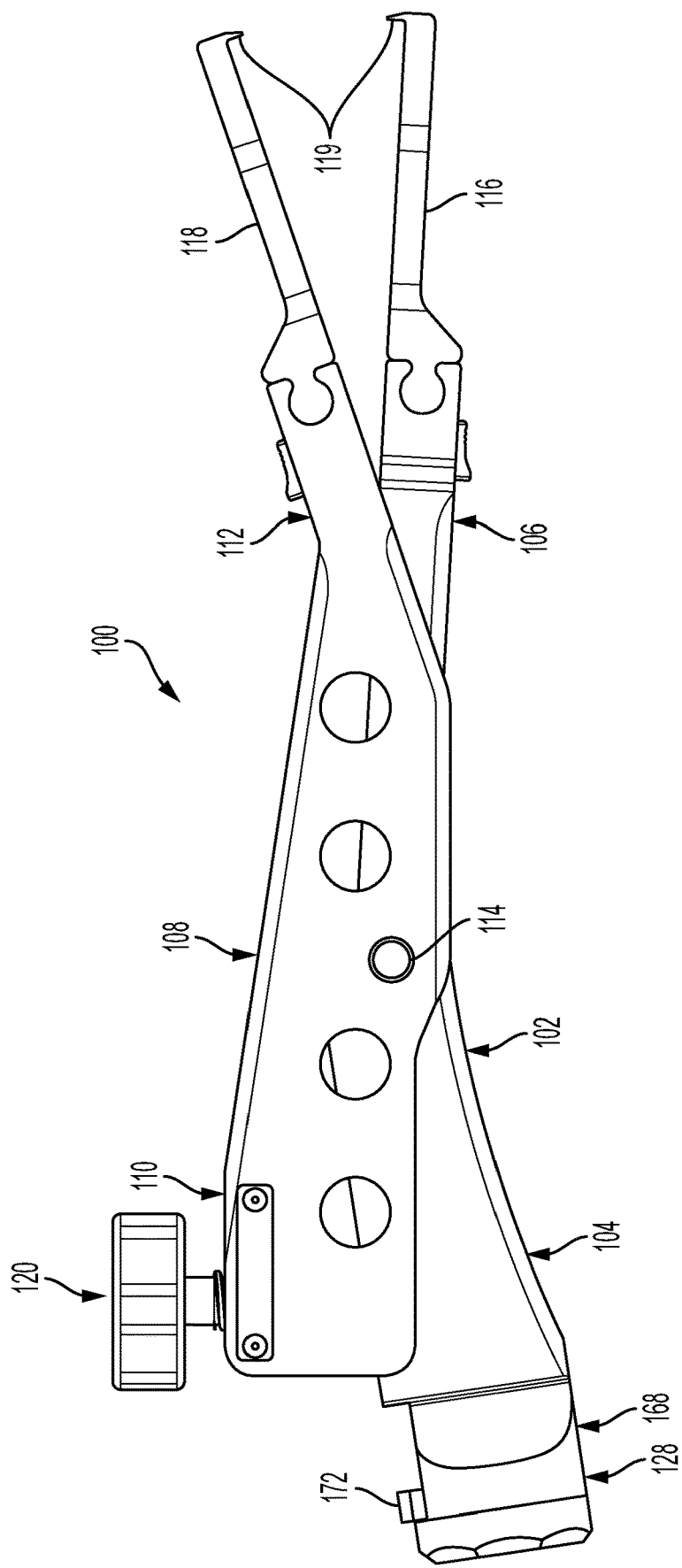
FIG. 2 is a side view of the implant extraction tool of FIG. 1.

In accordance with another exemplary aspect of the present embodiment, the implant extractor tool 100 can include first and second jaws 116, 118, as best shown in FIGS. 1 through 3. The first jaw 116 is preferably releasably attachable to the distal end 106 of the first arm 102 and the second jaw 118 is releasably attachable to the distal end 112 of the second arm 108. An exemplary mechanism for releasably attaching the first and second jaws 116, 118 to the distal ends of the first and second arms is described below in connection with FIGS. 10-12. At the distal end of each of the jaws 116, 118, there is provided a flange or lip 119 configured to engage an implant to be extracted. Alternatively, the first and second jaws can be permanently attached to the respective first and second arms or unitarily formed therewith.

The first and second jaws 116, 118 may be straight or the distal ends of the jaws may be offset or angled from the longitudinal axes of the first and second members 102, 108. The purpose for offsetting or angling the distal ends of the jaws 116, 118 is to allow them, in the context of glenosphere extraction, to reach around the humerus and other bone or soft tissue to access the glenoid area of the shoulder. Having a "double-angled offset" the present embodiment allows the implant extractor tool's main body to advantageously stay parallel to a direction of extraction of the glenoid implant or glenosphere and avoid interference with the surrounding bodily tissue. Without the double-angled offset, it is difficult to firmly clamp onto the implant and keep the extraction force in-line with the implant stem in the glenoid because of interference with the surrounding tissue. The shoulder is relatively a very tight area in which to fit instrumentation and the forces required for extraction can require stronger instruments thus increasing the size of the instrumentation. Some shoulders may be stiffer than others due to, but not limited to, prior surgeries or scar tissue, sutures, the natural range of a specific person's anatomy, etc., which limits the exposure in the surgery. Those situations would benefit from the use of the present implant extraction tool having double-angled offset jaws.

Straight jaws would be acceptable for use with the extractor tool when the exposure allows for a direct line of sight to the implant. That is, when no surrounding tissue would be present so as to obstruct or make it difficult for the extractor tool with straight jaws to grasp the implant to be extracted.

Figure 10:
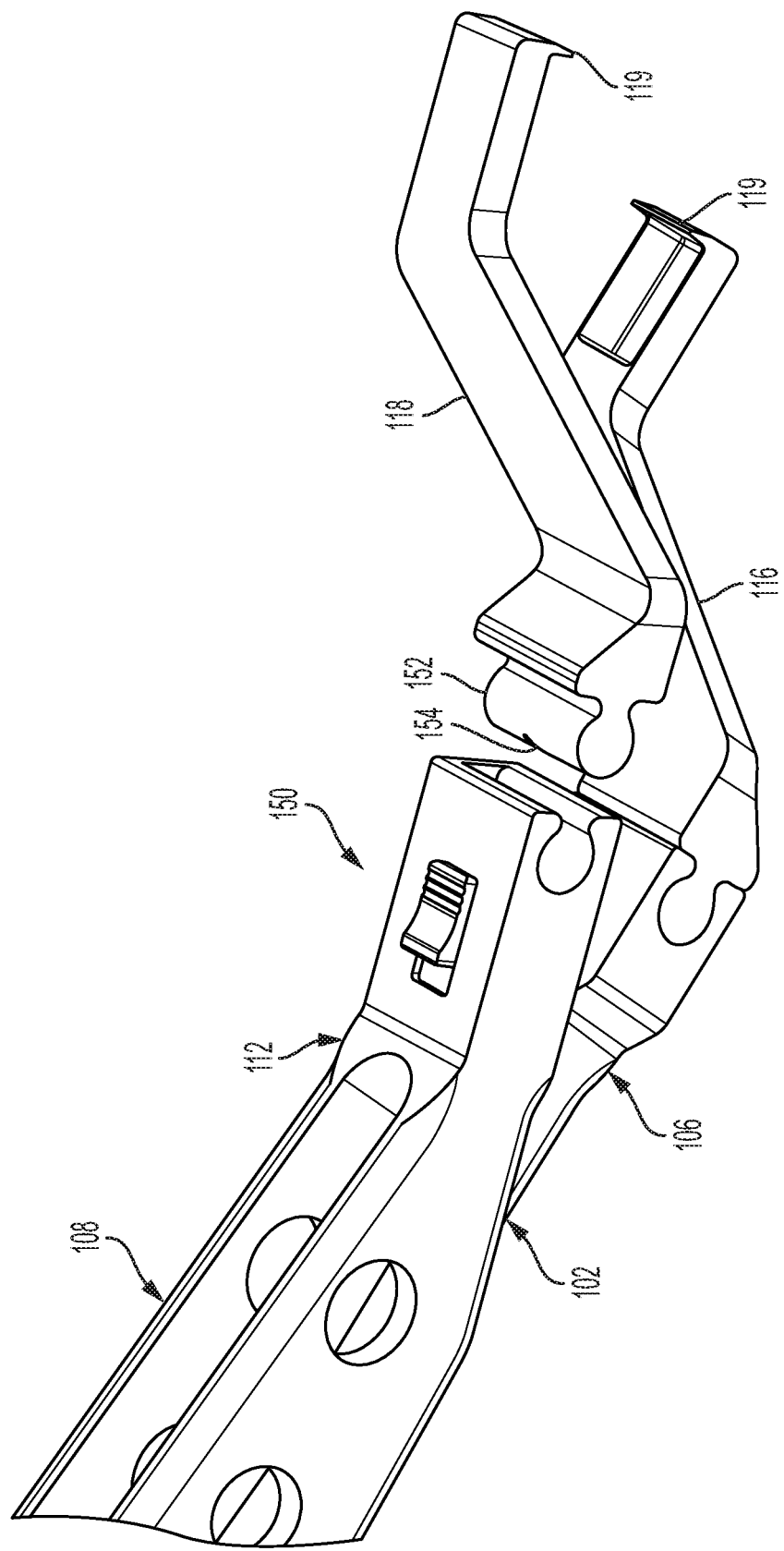
FIG. 10 is an enlarged perspective view of the distal ends of the first and second arms of the implant extraction tool of FIG. 1 with a jaw shown detached from the distal end of the second arm.
Figure 11:
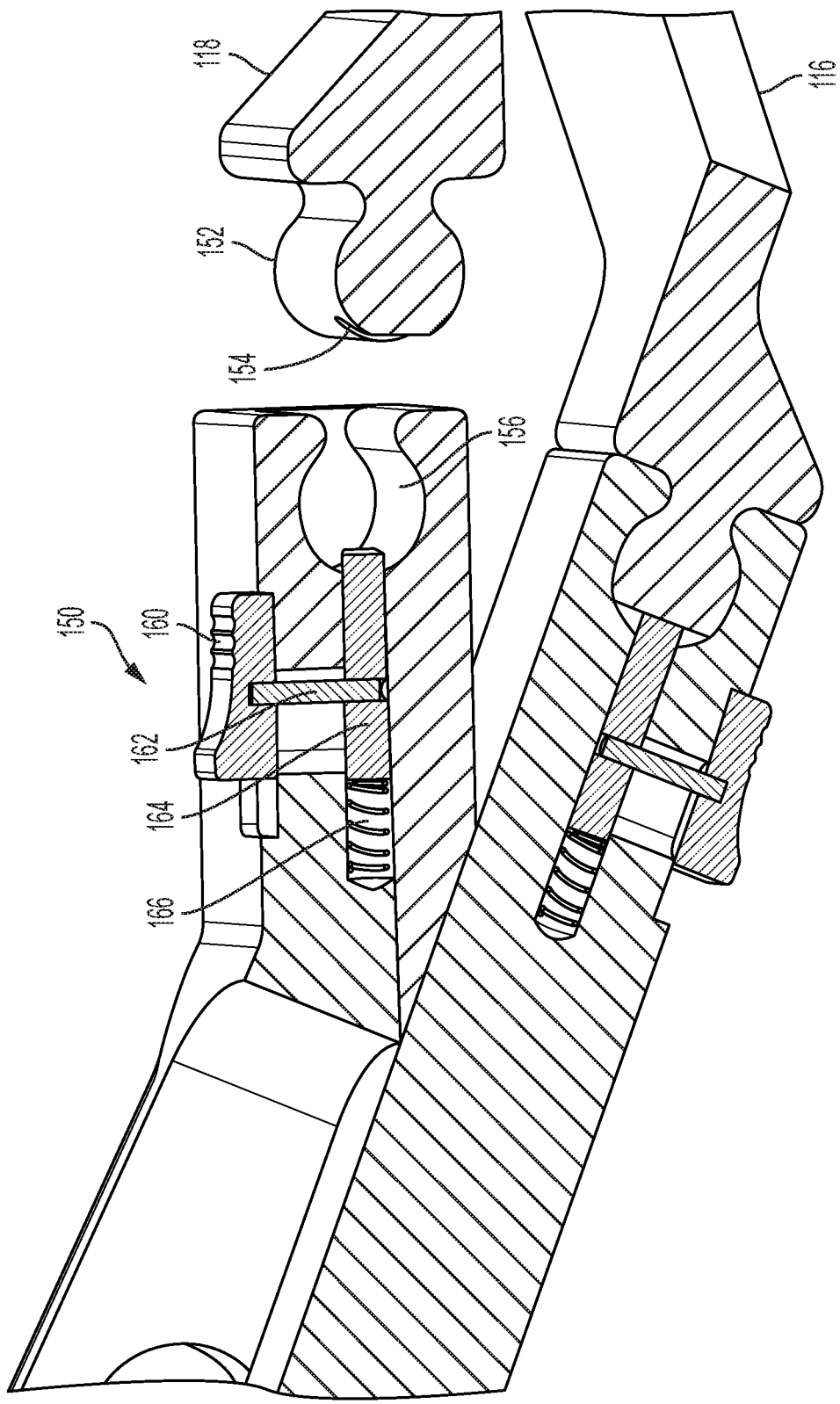
FIG. 11 is an enlarged cross-sectional view of a jaw attachment mechanism of the implant extraction tool of FIG. 10.
Figure 12:
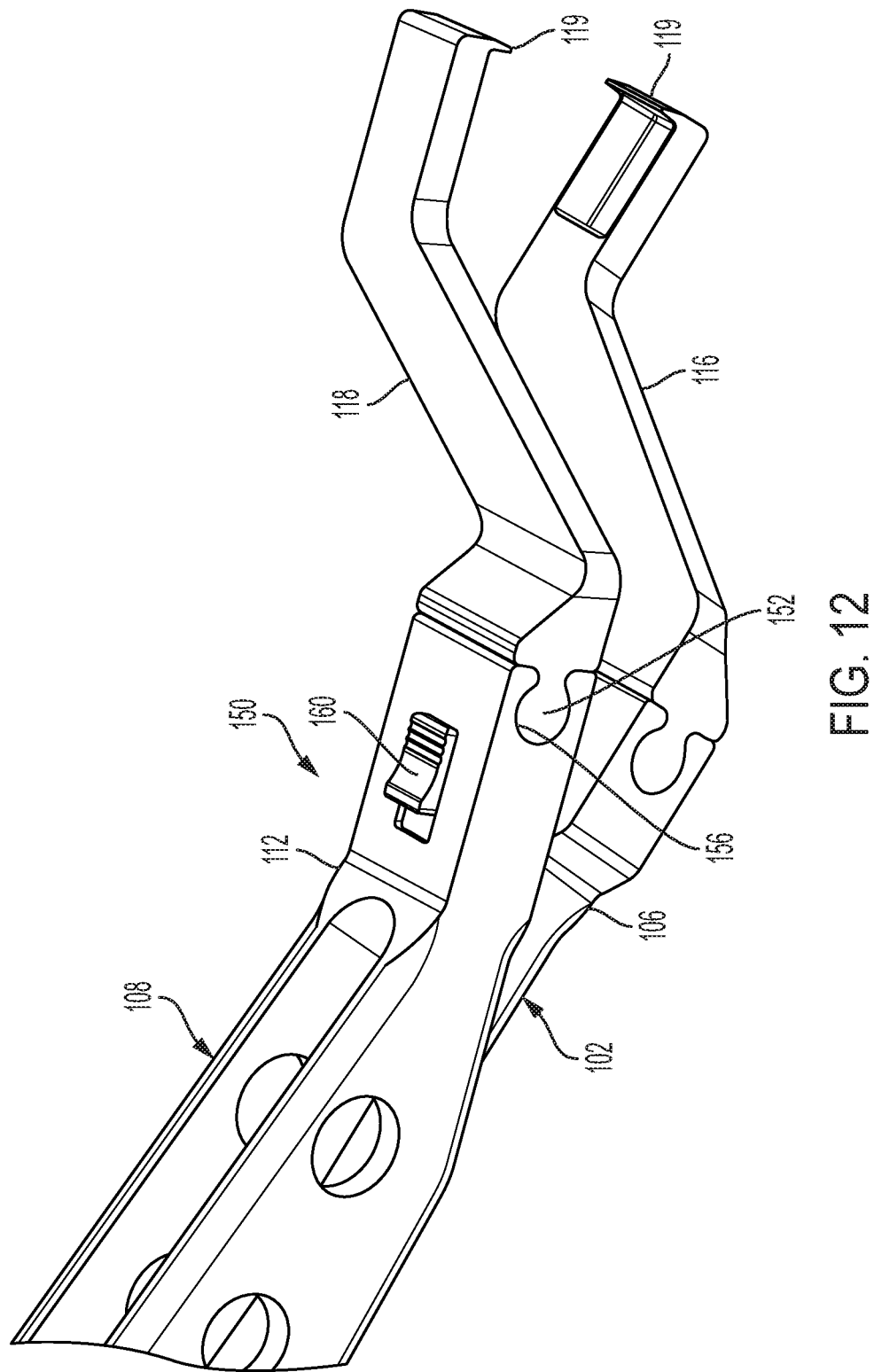
FIG. 12 is an enlarged perspective view of the distal ends of the first and second arms of the implant extraction tool of FIG. 1 with the jaws shown attached to the distal ends of the first and second arms.
Figure 13:
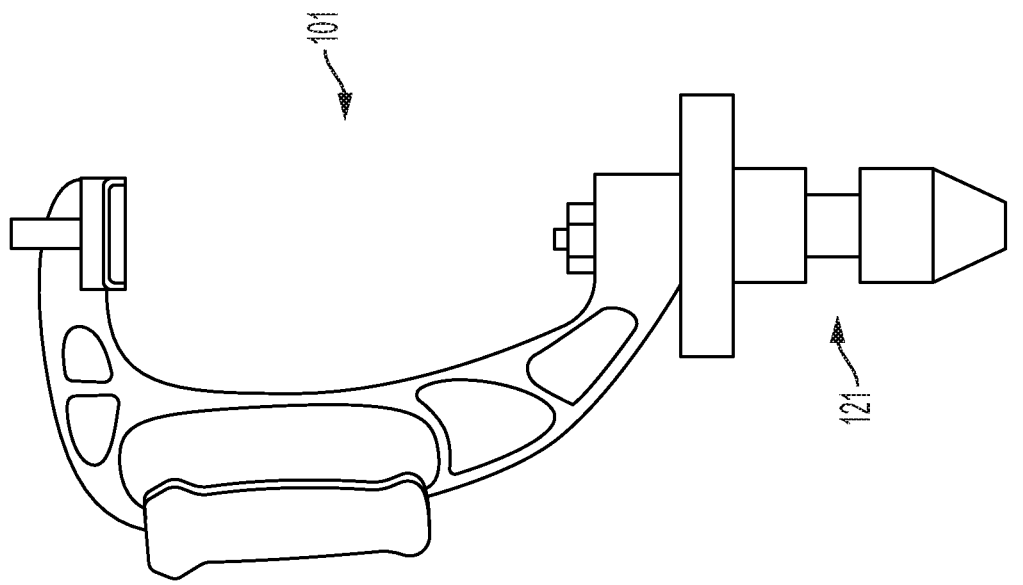
FIG. 13 is a side view of a C-frame extraction device suitable for use with the attachment mechanism of FIGS. 15-17.
Figure 14:
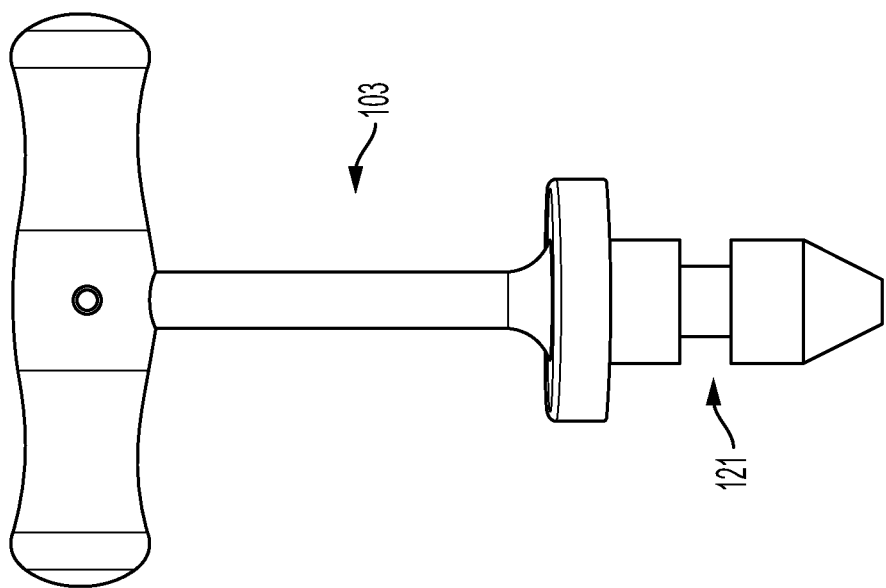
FIG. 14 is a side view of T-handle extraction device suitable for use with the attachment mechanism of FIGS. 15-17.

Referring to FIGS. 10 through 12, a latch 150 is provided on each of the first and second arms for releasably retaining respective first jaw 116 or second jaw 118. Each jaw includes a male connector 152 and notch 154 (FIGS. 10 and 11) provided at a most proximal end or top of the jaw. The male connector allows connection of the jaw to a respective female socket provided at the distal ends of the first and second arms 102, 108. The male connector is configured to be substantially matingly received in the female socket of the respective receptacles of the first and second arms.

Referring to FIG. 11, the latch 150 includes a slidable button 160 fixedly connected to a first end of a connector rod 162. The second end of the connector rod is connected to a retainer rod 164. A biasing member 166 biases a proximal end of the retainer rod 164 whereby the distal end of the retainer rod latchingly engages with the notch 154 provided in the male connector member 152 located at the proximal end of the respective first or second jaw 116, 118 to firmly retain them in the distal end(s) of the first or second arm, as shown in FIG. 12. In other words, by virtue of its connection to the retainer rod, the slidable button is normally biased forwardly into a latched state. When it is desired to release the slidable button from the latched state, the user slides the button rearwardly against the bias of the biasing member whereby the forward end of the retainer rod releases from engagement with the notch. At such time the jaw 116 or 118 may be slid from the female socket of the receptacle in order to remove the jaw from the implant extractor tool.

Referring to FIGS. 1 through 3, the implant extraction tool 100 further comprises an attachment mechanism 128 that releasably attaches an extraction device to a proximal end of one of the first and second arms (in the illustrated example the retaining mechanism is located at the proximal end 104 of the first arm 102). The extraction device may include, without limitation, a C-frame extraction device 101 (FIG. 13), a T-handle extraction device 103 (FIG. 14), or any suitable extraction device capable of applying an extraction force to the implant extractor tool 100. The general structures and functions of such extraction devices are known and therefore a detailed description is not necessary for a complete understanding of the subject disclosure.

Figure 15:
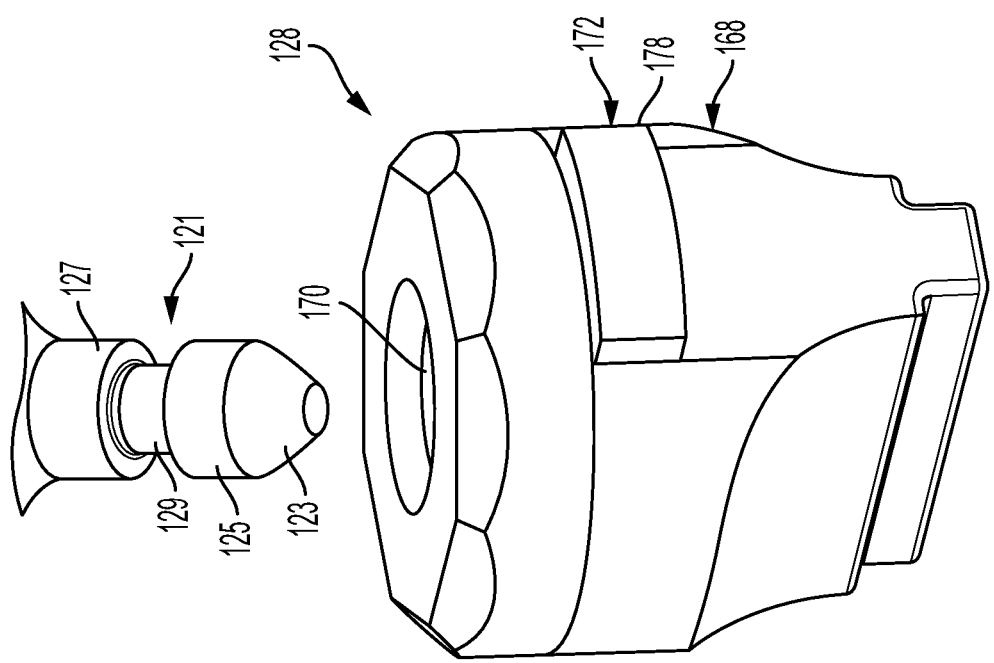
FIG. 15 is a perspective view of an attachment mechanism configured to releasably attach an extraction device to a proximal end of one of the first and second arms of the implant extraction tool of FIG. 1.

Extraction devices applicable to the present embodiments, however, include a male quick connect 121 which is configured to be releasably received in the attachment mechanism 128. As shown in FIG. 15, the quick connect 121 can include a tapered distal end 123 to facilitate insertion of the quick connect into the central cavity 170 of the attachment mechanism 128. The tapered distal end is contiguous with a first post 125 which is spaced from a second post 127 that is co-axial to the first post. An annular recess 129 is provided between the first post and the second post having a smaller diameter than first and second posts. The first and second posts may be circular, as shown, or they may assume other shapes, such as oval, and the like.

Figure 16:
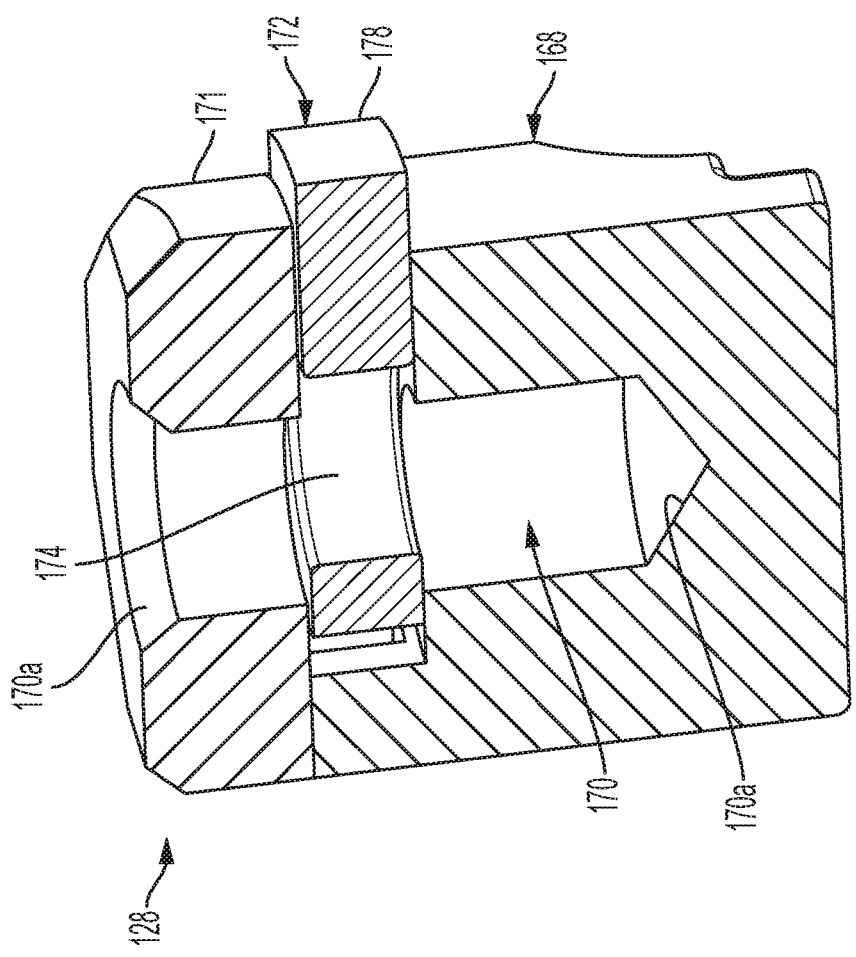
FIG. 16 is a cross-sectional view of the attachment mechanism of FIG. 15.
Figure 17:
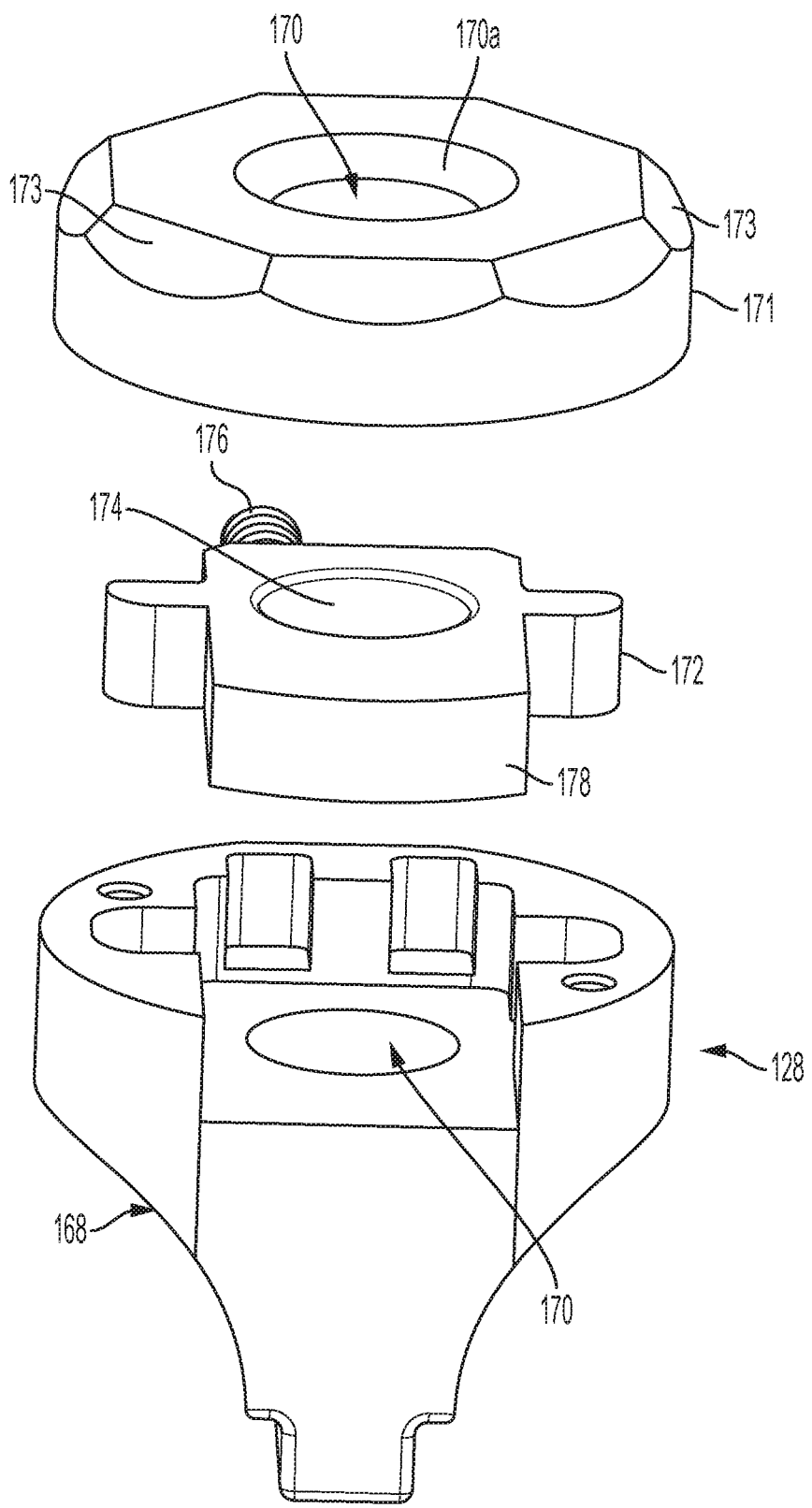
FIG. 17 is an exploded perspective view of the attachment mechanism of FIG. 15.

FIGS. 15 through 17 illustrate an exemplary attachment mechanism in accordance with the subject disclosure. The attachment mechanism 128 is attachable to the proximal end of the first arm 102 or the second arm 108. In the illustrated example shown in FIGS. 1 through 3, the attachment mechanism is attached to the first arm 102. The attachment mechanism 128 includes a retaining housing 168 having the central cavity 170 for receiving an extraction device connection, e.g. quick connect 121. The attachment mechanism further includes a locking mechanism 172, a biasing member 176, and a cap 171.

The locking mechanism 172 is moveable between first and second positions relative to the retaining housing 168. The locking mechanism has a through hole 174 (FIG. 16) for receiving an extraction device quick connect 121. The biasing member 176 biases the locking mechanism towards a first position whereby the locking mechanism 172 moves to partially occludes the central cavity 170 from freely allowing the passage of an extraction device quick connect 121 to pass through. For example, in the first position, a central longitudinal axis of the through hole 174 is offset from a central longitudinal axis of the central cavity 170 whereby the locking mechanism engages the annular recess 129 of the quick connect to retain the quick connect in the central cavity. Additionally, in the first position, the locking mechanism defines a button end 178 that extends proud laterally of the retaining housing 168 under the bias of the biasing member 176. In the second position, when the button end 178 of the locking mechanism is depressed by a user, a central longitudinal axis of the through hole 174 is aligned with the central longitudinal axis of the central cavity 170 such that the locking mechanism disengages from the annular recess of the quick connect and the quick connect may be inserted into or removed from the central cavity.

The cap 171 has an opening 170a which is contiguous with the central opening 170 to facilitate insertion of the distal end 123 of the quick connect 121 into the central opening. The cap can also include a plurality of chamfered edges 173 circumscribing the central opening 170. The central opening 170, opening 170a and the through hole 174 may be circular, as shown, or they may assume other shapes, such as oval, and the like. The central opening can be a counterbore having a tapered bottom end adapted to substantially mate with the tapered distal end 123 of the quick connect 121 to provide a stable fit of the quick connect within the central opening.

Assembly of the implant extractor tool 100 may be achieved as follows. Referring first to FIG. 11, the user attaches the appropriate jaws to the distal ends 106, 112 of the first and second arms 102, 108. Beginning with the first arm 102, the user slides the slidable button 160 and thus the retainer rod rearwardly against the bias of biasing member 166. This, in turn, fully opens the female socket 156 whereby the female socket may receive the male connector member 152 of the jaw 116. The user then slides the male connector member 152 of the jaw fully into the female socket 156. Once the male connector member is seated within the female socket, the biasing member 166 moves the retainer rod 164 forwardly until its distal end engages the notch 154 provided in the male connector member 152 of the jaw 116 to lock the jaw to the distal end 106 of the first arm 102. The user repeats the foregoing process to attach the jaw 118 to the distal end 112 of the second arm 108. In order to remove a jaw from the first or second arm, the button 160 must be moved against the bias of biasing member 166 whereby the distal end of the retainer rod 164 retracts from the notch 154 and the male connector member can be slid out of the female socket.

Referring next to FIGS. 1 through 3 and 15 through 17, the user grasps the implant extractor tool 100 and depresses protruding button end of the locking mechanism 172 of the attachment mechanism 128. Depressing the locking mechanism 172 moves it from occluding the central cavity 170 whereby the extraction device quick connect 121 may be inserted into the central cavity. The user then releases the actuator 170 whereby the locking mechanism engages the annular recess 129 of the quick connect and is retained within the attachment mechanism 128.

The subject disclosure also provides a method for extracting an implant using the above-described extractor tool 100. After assembling the tool as described above, the method comprises grasping the tool such that the palm of the user's hand contacts the first arm 102 and the user's fingers wrap around the second arm 108 or, alternatively, vice versa. The user then manipulates the tool 100 to place the jaws 116, 118 on either side of the implant to be extracted with the lips 119 of the jaws aligned to engage the rear side, underside, etc. of the implant. Once the lips of the jaws are in proper alignment with the implant, the user depresses the knob 144 of the actuator 126 (FIGS. 6 through 9) with his or her thumb or index finger. Depressing the knob moves the latch 140 against the bias of the biasing member 148 such that the teeth 142 of the latch move from a first position (FIG. 8) engaging the threads of the threaded shaft 130 of the adjuster 122 to the second position such that the teeth of the latch disengage the threads of the threaded shaft of the adjuster.

Once the teeth of the latch 140 disengage the threads of the threaded shaft 132, the biasing member 124 (FIGS. 6 through 8) urges the adjuster 122 forwardly whereby the domed distal end 136 of the adjuster contacts the concave seat 137 and moves the proximal ends of the first and second members away from one another and the lips 119 of the jaws 116, 118 into engagement with the implant. The user then releases the knob 144 whereby the teeth of the latch 140 return to the first position (FIG. 8) engaging the threads of the threaded shaft 132 of the adjuster 122. So constructed, the extractor tool 100 provides one-handed operation for engaging the extractor tool with the implant. Lastly, if necessary, turning the control knob 134 of the adjuster 122 in a first direction when the latch 140 is in engagement with the adjuster causes the first and second jaws 116, 118 to further tighten about an object to be extracted (e.g., to perform fine tuning adjustments) owing in part due to the splines 142 on the latch. The user may then use an extraction device connected to the proximal end 104 of the first arm 102 to exert extraction force to remove the implant from the bone in which it is embedded.

Figure 18:
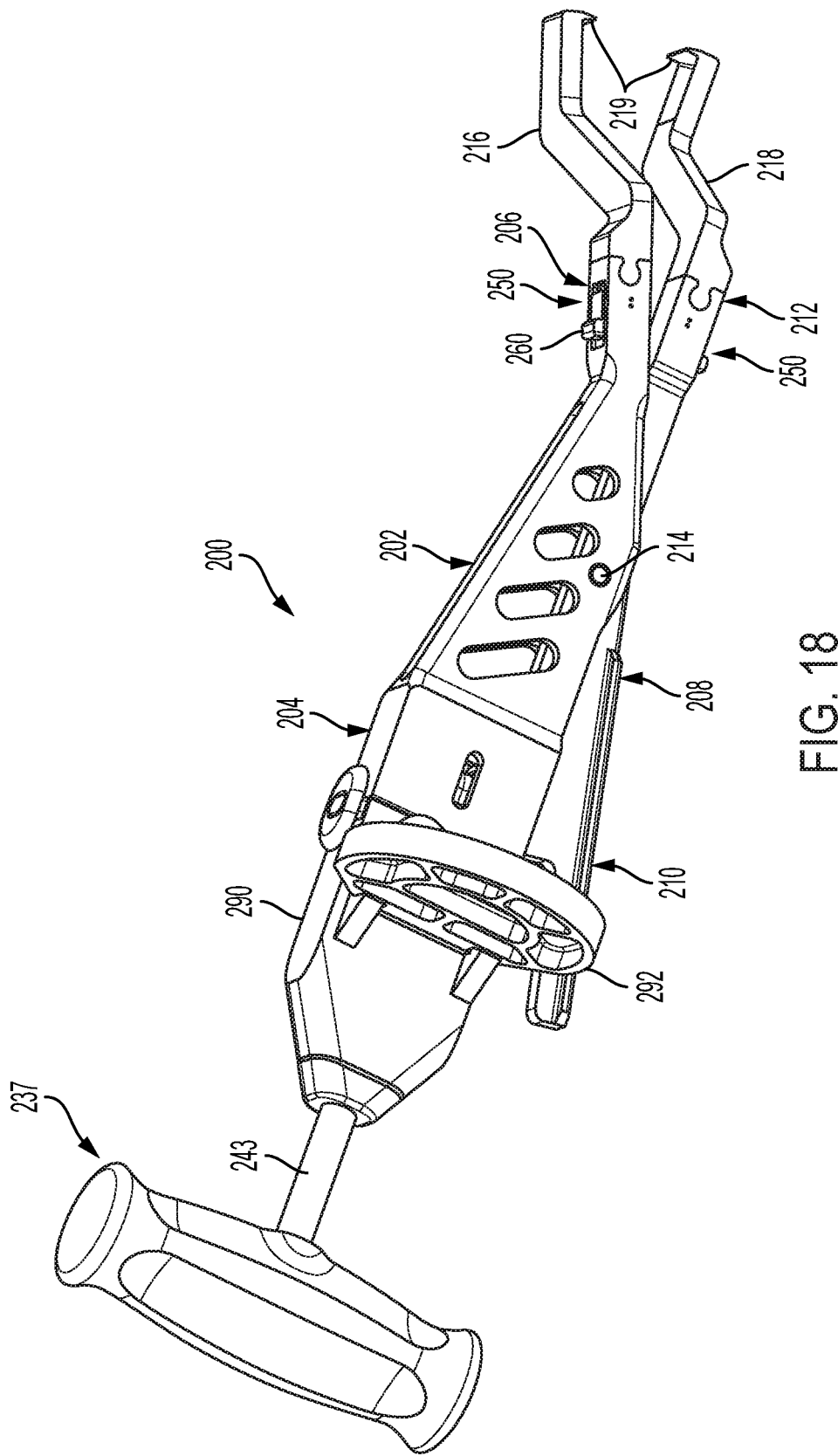
FIG. 18 is top perspective view of an implant extraction tool in accordance with another exemplary embodiment of the subject disclosure.
Figure 19:
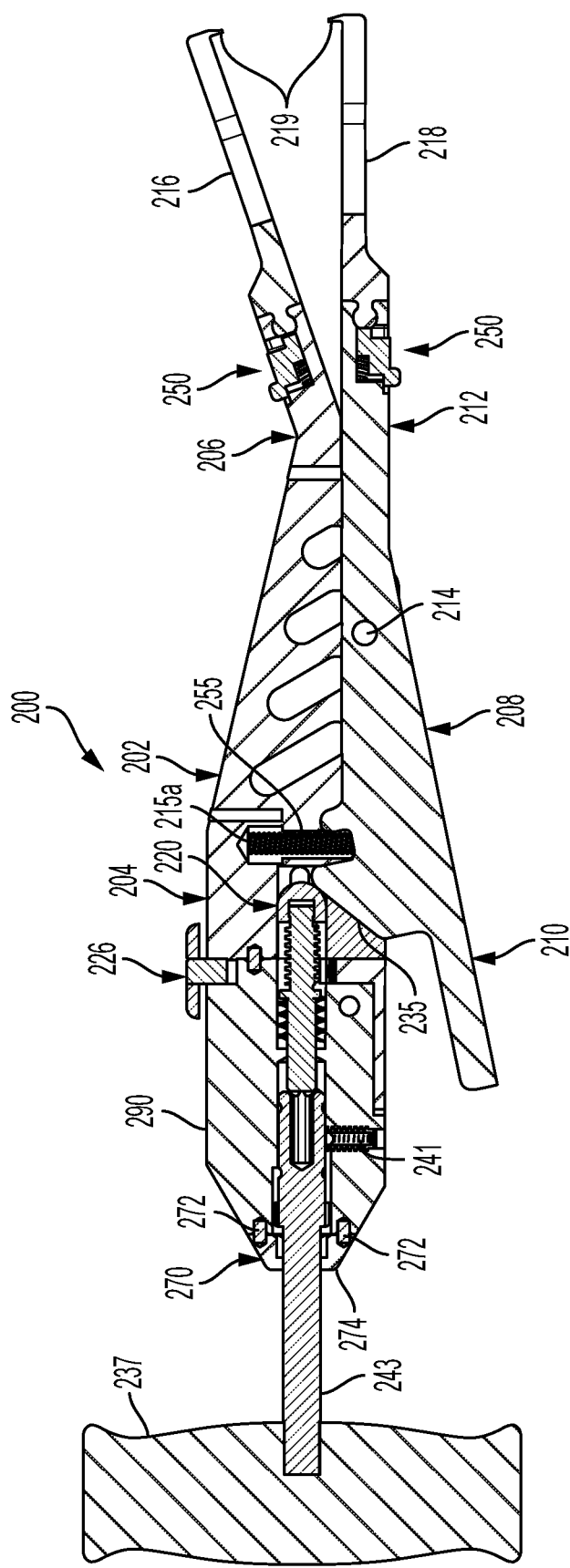
FIG. 19 is a cross-sectional view of the implant extraction tool of FIG. 18.

FIGS. 18 and 19 illustrate an implant extractor tool 200 in accordance with another exemplary embodiment of the present disclosure. The implant extractor tool 200 comprises a first arm 202 having a proximal end 204 and a distal end 206 (see also FIGS. 20A and 20B). The extractor tool 200 further comprises a second arm 208 having a proximal end 210 and a distal end 212 (see also FIGS. 21A and 21B). The second arm is pivotably connected to the first arm at pivot pin 214.

Figure 20A:
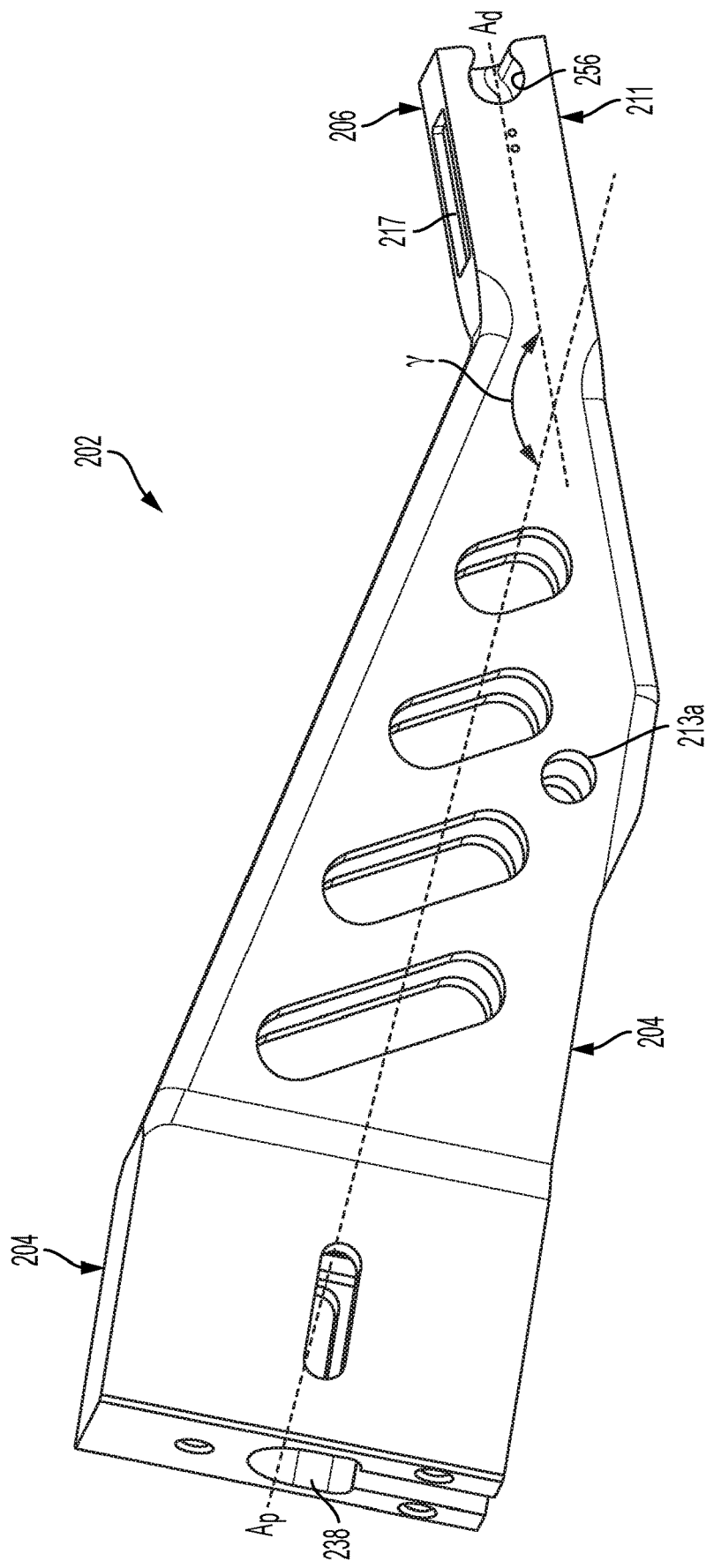
FIG. 20A is a perspective view of a first arm of the implant extraction tool of FIG. 18.
Figure 20B:
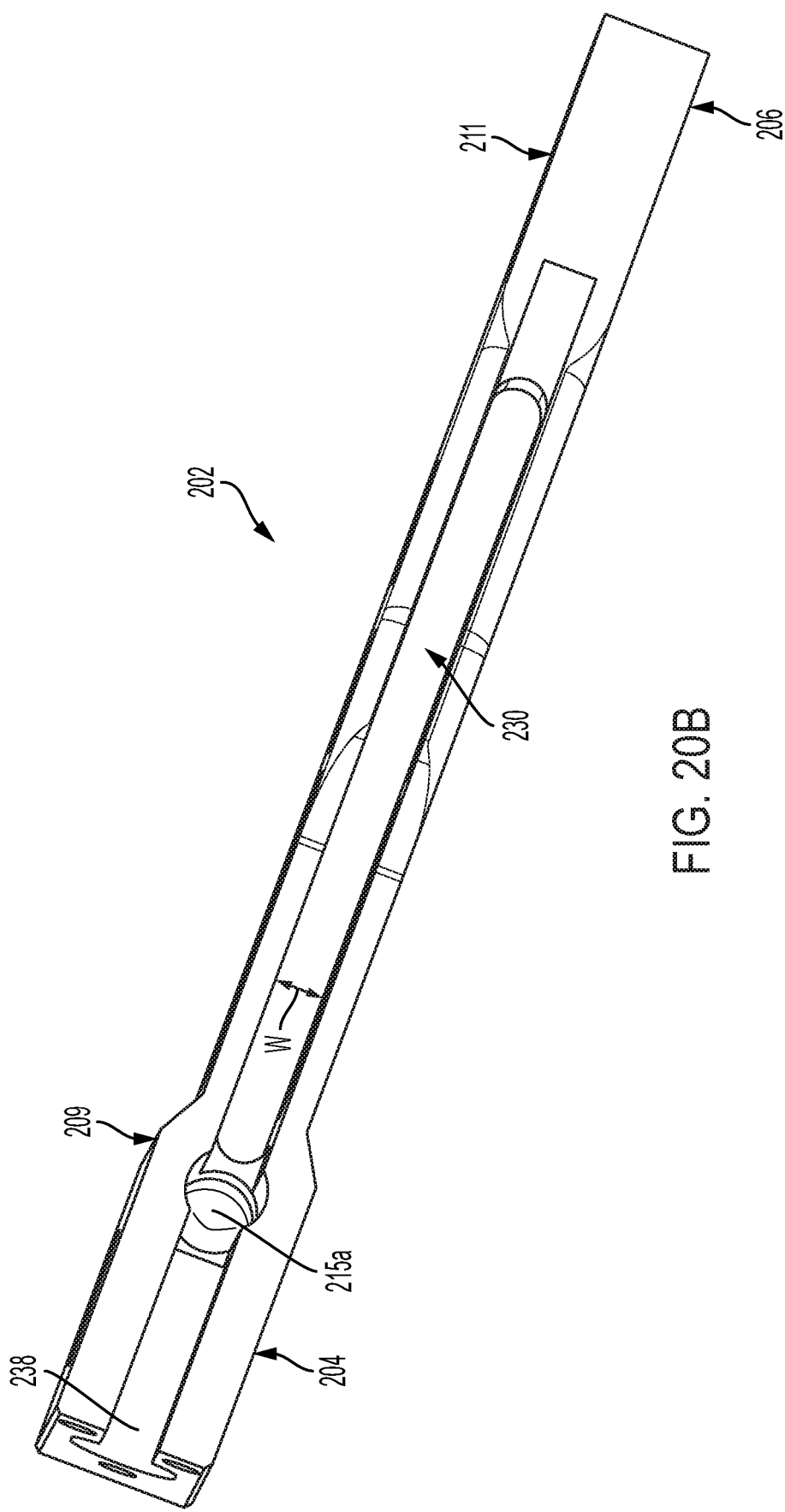
FIG. 20B is a bottom perspective view of the first arm of the implant extraction tool of FIG. 18.

FIGS. 20A and 20B best illustrate an exemplary construction of the first arm 202. In addition to the proximal end 204 and the distal end 206, the first arm has a generally open central region 230 configured to receive the second arm 208. That is, the open central region is, e.g., an opening or through hole that faces in the anterior direction of the first arm. The opening is an elongated opening that substantially spans the length of the midportion of the first arm. The first arm is configured to have an anterior facing side with depending lateral sides so as to form a substantially hollow U-shaped frame. The lateral sides are spaced apart a width "W" sufficient to receive the second arm therein.

The first arm 202 is an elongated arm including a proximal arm segment 209 and a distal arm segment 211 having a longitudinal axis "$A_d$" at an angle α of about 90 to 180 degrees, and preferably about 160 to 170 degrees, including 100, 110, 120, 130, 140, 150, 165, and 175 degrees relative to a longitudinal axis "$A_p$" of the proximal arm segment. The first arm also includes a through hole 213a about its midportion having a longitudinal axis substantially perpendicular or transverse to the longitudinal axis of the first arm. Further, the through hole 213a faces a lateral side of the first arm and is alignable with a through hole 213b (FIGS. 21A and 21B) of the second arm 208 to receive the pivot pin 214.

Additionally, the first arm includes a recess 215a (FIG. 20B) for receiving a first end of a biasing member 255 (FIGS. 19 and 25) for biasing the first and second arms 202, 208. The recess, e.g., a counterbore, is a posteriorly facing recess and is positioned adjacent the opening 230. The first arm further includes a proximally facing through hole 238 in the proximal arm segment 209 for receiving an adjuster 222, further described below.

The first arm can include a receptacle 256 about its distal end. The receptacle 256 can be configured similarly to receptacle 156 described in the above embodiment for connecting to a jaw. Further, the first arm includes an anteriorly facing opening 217 in the distal end segment 211 for receiving a latch 250 (FIG. 18) for releasably retaining the first jaw in the receptacle 256. Latch 250 is constructed and functions substantially the same as latch 150 described above.

Jaws 216, 218 can attach to respective receptacles at the distal ends of the arms, similarly to that discussed in the above embodiment, and are illustrated as being offset jaws similar in construction to the offset jaws 116, 118 of the implant extractor tool 100. It is understood, however, that the jaws may be straight jaws or may have some other configuration.

The proximal end 204 of the first arm is adapted for connection to a housing 290 which forms an extension of the first arm. The housing 290 is configured to receive a shaft 243 of an extraction handle 237, the structure and functions of which are described below. In addition, a strike plate 292 extends from one of the first or second arms (in the illustrated example of FIG. 18, the strike plate 292 is attached to the first arm 202, in particular the housing 290). The strike plate 292 is provided to be struck, typically on its distal surface, by a striking tool such as a mallet, hammer or the like, in order to extract an implant from bone, as described below.

Figure 21A:
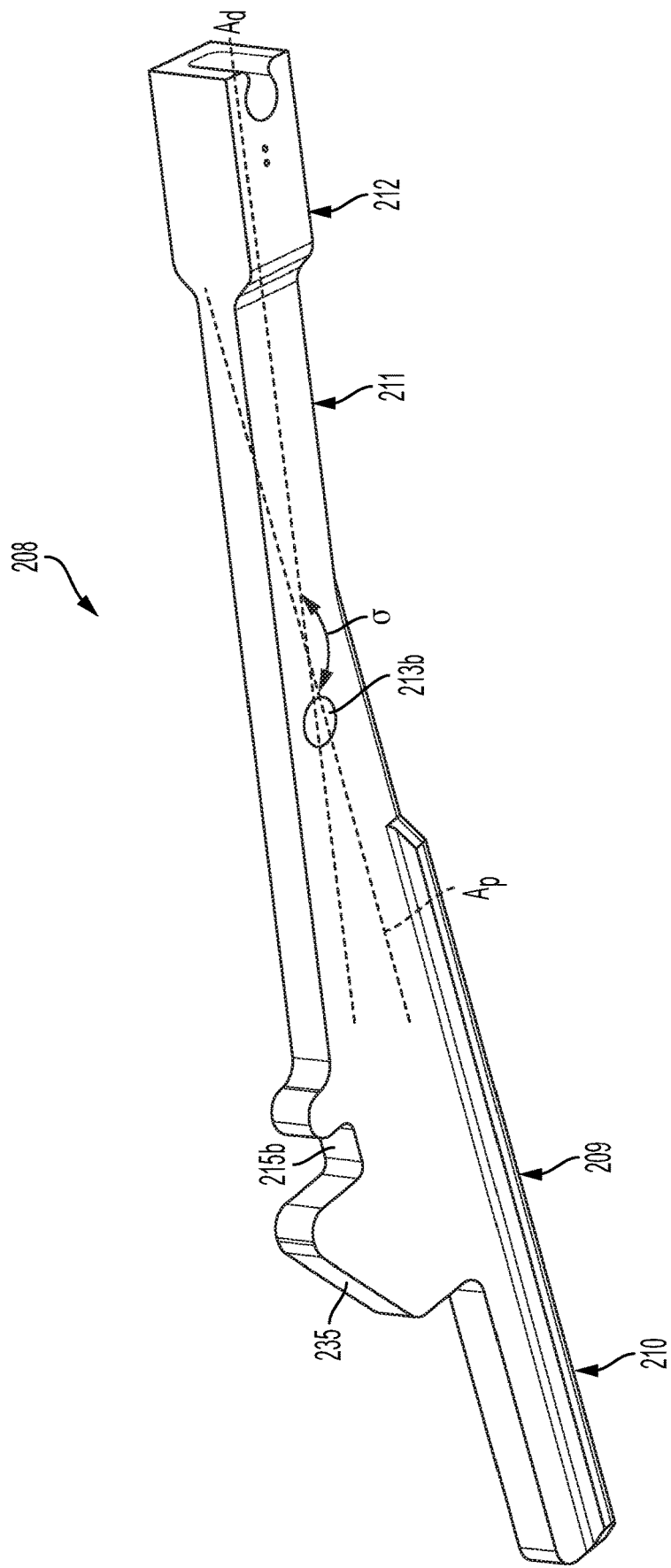
FIG. 21A is a perspective view of a second arm of the implant extraction tool of FIG. 18.
Figure 21B:
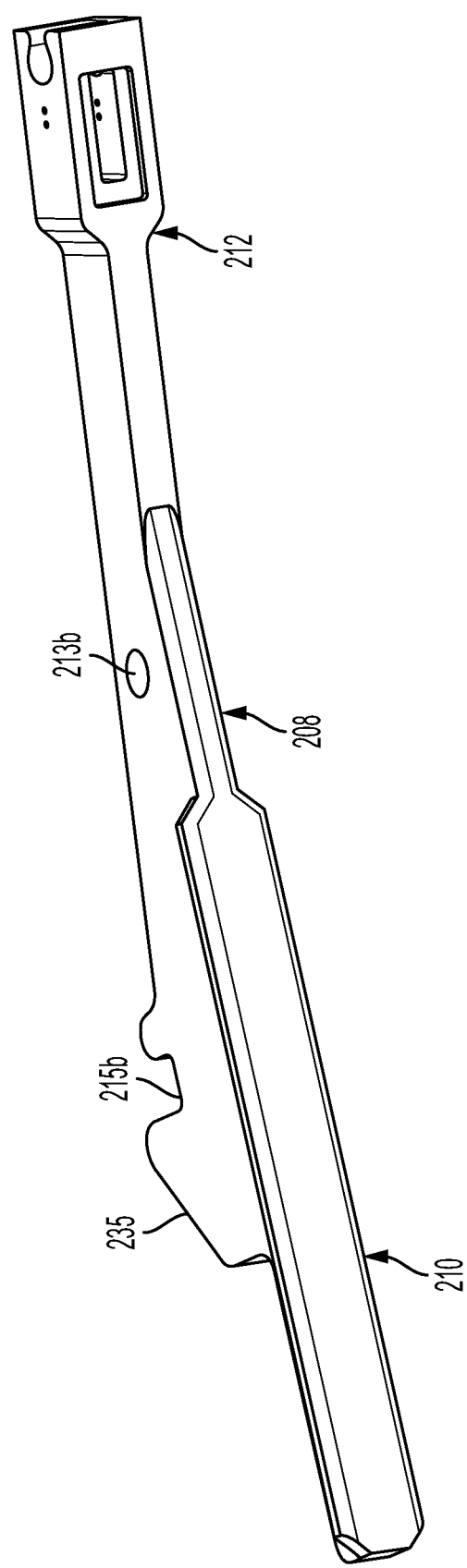
FIG. 21B is another perspective view of a second arm of the implant extraction tool of FIG. 18.

FIGS. 21A and 21B best illustrate an exemplary construction of the second arm 208. The second arm 208 can be of unitary construction wherein the distal end 212 is configured to releasably receive a second jaw 218. The second arm includes a proximal arm segment 209 and a distal arm segment 211 having a longitudinal axis "$A_d$" at an angle α of about 90 to 180 degrees, and preferably about 160 to 180 degrees, including 100, 110, 120, 130, 140, 150, 165, 170, and 175 degrees relative to a longitudinal axis "$A_p$" of the proximal arm segment. The angled configuration of the proximal and distal arm segments provide for greater expansion between the distal ends of the first and second arms. The second arm includes the through hole 213b for receiving the aforementioned pivot pin 214. In addition, the second arm has a recess 215b for receiving the biasing member 255 for biasing the first and second arms 202, 208 toward the open or retracted position. The recess 215b is positioned about a midportion of the proximal arm segment 209. In addition, the second arm includes a sloped cam surface 235 disposed about a midportion of the proximal arm segment configured for engagement with a bulbous end 232 of the adjuster 222, as described below.

The implant extractor tool 200 further comprises an adjustment mechanism 220 (FIGS. 19, 22, 25 and 26) that is operatively connected to and housed completely within one of the first and second arms 202, 208 for engaging the other of the first and second arms. In the illustrated example, the adjustment mechanism, including the below-described adjuster 222, is operatively connected to and housed within the first arm 202.

Figure 23:
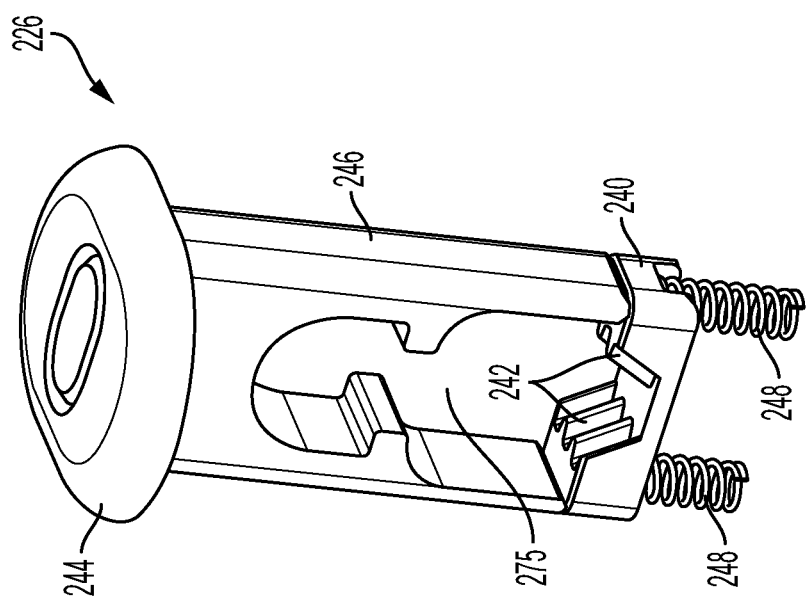
FIG. 23 is a perspective view of the actuator of the implant extraction tool of FIG. 18.

The adjustment mechanism 220 includes an adjuster 222, which is best shown in FIGS. 22 and 25. The adjuster 222 comprises a threaded portion 230, a splined shaft 231 and a bulbous end 232. FIGS. 22, 23 and 25 show that the adjuster 222 extends through a through hole 275 provided in a midportion of an actuator 226, further discussed below.

A biasing member 224 biases the first and second arms in concert with the actuator of the implant extractor tool 200. According to an aspect, the biasing member 224 surrounds the splined shaft 231 and is adjacent a flange 253 which separates the splined shaft from the threaded portion. The biasing member can be, e.g., a spring or an annular elastomer. In the illustrated embodiment, the biasing member is a wave spring.

As best shown in FIGS. 22, 23 and 25, the implant extraction tool 200 comprises the actuator 226, which is mounted to the first arm 202. The actuator 226 is moveable between a first position (FIGS. 19, 22, 25 and 26) and a second position. The first position is an engaged position that prevents movement of the first and second arms under the bias of the biasing member 224. The second position is a released position that permits movement of the first and second arms under the bias of the biasing member 224. The actuator 226 comprises an actuation button 244 and a shaft 246 extending from the actuation button. A latch 240 is disposed about a distal end of the shaft 246 and at least one actuator biasing member 248 biases the latch. The at least one actuator biasing member may be, e.g., a spring or an elastomer. The latch 240 is configured to engage the adjuster 222 in the first position and release the adjuster in the second position.

As shown in FIG. 23, the latch 240 is provided with teeth or splines 242 that releasably engage the threads of the threaded portion 230 of the adjuster 222. The teeth or splines 242 face in a generally anterior direction and configured to matingly engage the threads of the threaded portion 230 of the adjuster. That is, the teeth 242 face substantially inwardly and upwardly to engage the threads of the threaded portion of the adjuster.

Figure 26:
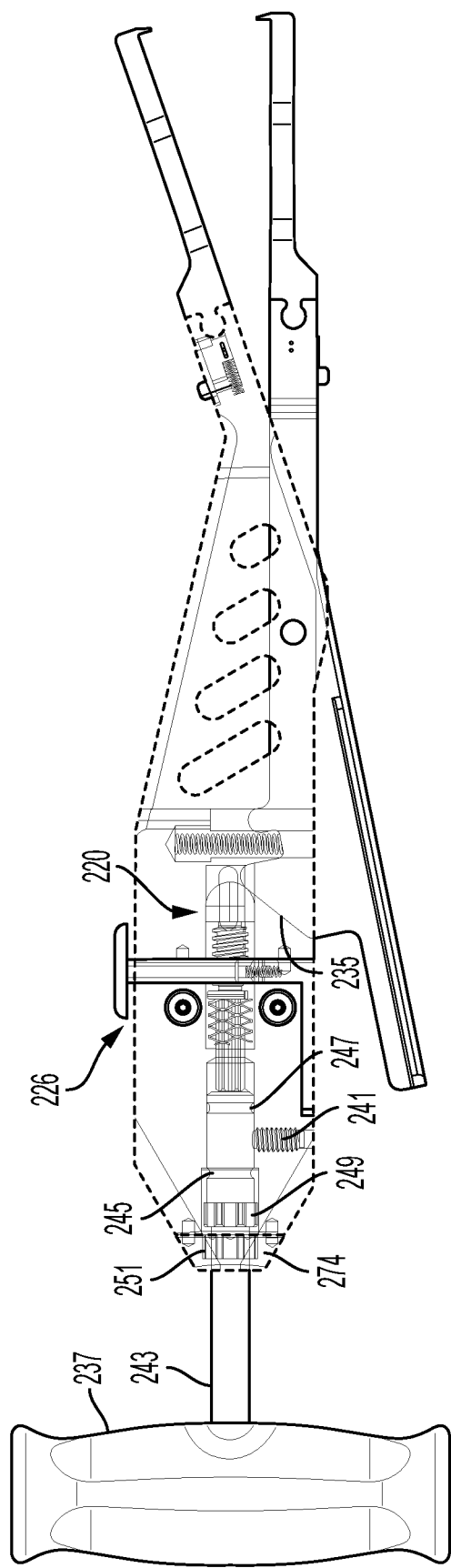
FIG. 26 is a side view of the implant extraction tool of FIG. 18 with certain elements shown in phantom for purposes of clarity.

FIGS. 19, 21A, 21B, 25 and 26 show that the cam surface 235 engages with the adjuster 222. In the illustrated example, the cam surface 235 is provided on the proximal segment 209 of the second arm 208. Referring to FIGS. 19, 25 and 26, the bulbous end 232 of the adjuster cams against the cam surface 235 when the actuator assembly 224 is in the second position to move proximal ends of the first and second arms 202, 208 away from one another and the first and second jaws 216, 218 toward one another to grip an implant to be extracted.

According to an aspect, one of the first and second arms 202, 208 includes an attachment mechanism 270 comprising at least one fastener 272 (FIG. 19) releasably attaching an extraction device or handle 237 to its proximal end. In the illustrated example, the attachment mechanism 270 is a cap 274 securable to the housing 290 which, in turn, is secured to the first arm 202.

Figure 24A:
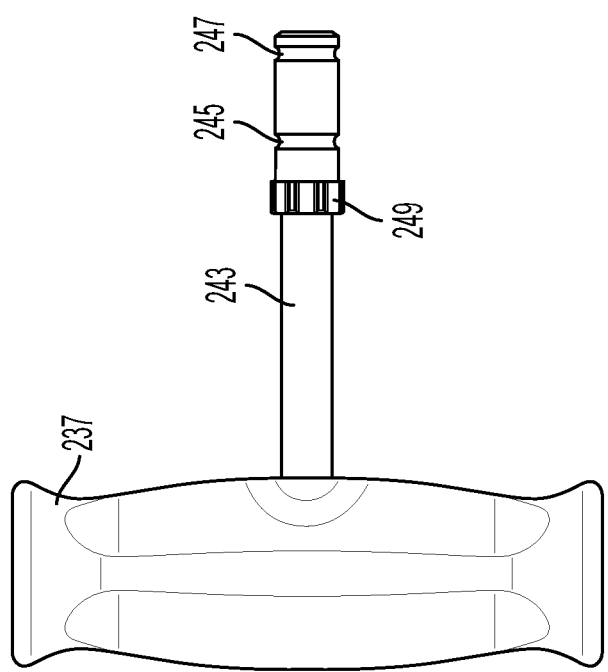
FIG. 24A is a side view of an extraction handle and shaft operable to cooperate with the adjustment mechanism of FIG. 22.
Figure 24B:
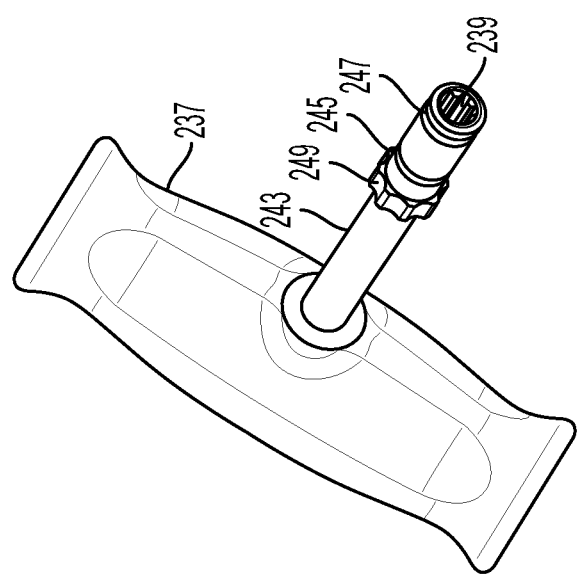
FIG. 24B is a bottom perspective view of the extraction handle and shaft of FIG. 24A.

FIGS. 24A, 24B and 25 best illustrate the construction of the extraction handle 237 and handle shaft 243. As shown in FIGS. 24A and 24B, the extraction handle 237 and handle shaft form a "T" where the handle is configured to be gripped and manipulated by a user. Shaft 243 projects from the handle 237 and is provided with a plurality of spaced apart annular grooves, namely, a first annular groove 245 and a second annular groove 247, as well as splines 249, the functions of which are described below. As shown in FIGS. 24B and 25, a distal end of the handle shaft 243 has a splined socket 239 configured to cooperatively engage the splined shaft 231 of the adjuster 222.

As shown in FIGS. 19, 25 and 26, the implant extractor tool 200 further comprises a radially inwardly disposed detent 241 provided in the housing 290 which is operable to releasably engage the shaft 243 of the extraction handle. The handle shaft 243 is operable in concert with the detent 241 to facilitate one or more modes of operation of the extractor tool, such as a first mode, a second mode and a third mode. The detent can be e.g., a set screw or the like.

A first mode allows the user to engage or connect the implant extractor tool to the implant. In the first mode, the detent 241 engages a first annular groove 245 in the handle shaft 243 and the splined socket 239 of the handle shaft is cooperatively engaged with the splined portion 231 of the adjuster 222. In this mode, the bulbous end 232 of the adjuster is advanced along the cam surface 235 which pushes the contacted second arm 208 to tighten the clamping force of the jaws 216, 218 to the implant.

Referring to FIGS. 25 and 26, the second mode allows the handle 237 to rotate freely as desired by the user. In the second mode, the detent 241 is positioned anywhere between the first annular groove 245 and a second annular groove 247 in the handle shaft. Concurrently, the splined socket 239 of the handle shaft 243 is disengaged from the splined portion 231 of the adjuster 222, and splines 249 of the handle shaft are similarly disengaged from splines 251 provided in the cap 274 of housing 290. This mode allows the user to reposition the handle relative to the extractor tool for comfort and ease of extraction.

Still referring to FIGS. 25 and 26, the third mode allows the user to rotate the handle 237 and the extractor tool 200 in concert. For this mode the user pulls back on the handle 237 until the detent 241 engages the second annular groove 247 and the splines 249 engage the splines 251 of the cap 274. In this position, the handle 237 is rotationally locked relative to the remainder of the implant extractor tool 200, whereby the user may twist the handle and thus the remainder of the implant extractor tool to dislodge the implant form the bone in which it is embedded.

The subject disclosure also provides a method for extracting an implant using the above-described implant extractor tool 200. The method comprises grasping the tool such that the palm of the user's hand contacts second arm 208 and the user's fingers wrap around the first arm 202 or, alternatively, vice versa. The user then manipulates the tool 200 to place the jaws 216, 218 on either side of the implant to be extracted with the jaw lips 219 (FIGS. 18 and 19) of the jaws aligned to engage the implant. Once the lips of the jaws are in proper alignment with the implant, the user depresses the actuation button 244 of the actuator 226 (FIG. 25) with his or her index finger against the bias of the biasing member(s) 248. With the actuation button 244 depressed, the teeth 242 of the latch 240 move from the first position engaging the threads of the threaded portion 230 of the adjuster 222 to the second position such that the teeth of the latch disengage the threads of the threaded portion 230 of the adjuster 222.

Once the latch 240 is in the second position, the biasing member 224 urges the adjuster 222 forwardly. Accordingly, the bulbous end 232 of the adjuster slidingly engages the cam surface 235 to move the proximal ends of the first and second members 202, 208 away from one another and the first and second jaws 202, 208 toward one another to grip an object to be extracted. So constructed, the extractor tool 200 provides one-handed operation for engaging the extractor tool to the implant and allowing the extractor tool to tighten about the implant to be extracted. Thereafter, the handle shaft 243 may be pushed forwardly toward the first and second members 202, 208 until the detent 241 engages the first annular groove 245 and the splined socket 239 at the distal end of the handle shaft 243 is cooperatively engaged with the splined shaft 231 of the adjuster 222. At this point, the user may turn the handle 237 so as to rotate the adjuster 222, thereby tightening the grip of the first and second jaws 216, 218 about the implant.

The user then withdraws the handle 237 until the detent 241 is between the first and second annular grooves 245, 247 and rotates the handle to a comfortable position. Once at a comfortable position, the user further withdraws the handle until the splines 249 of shaft 243 are engaged with splines 251 provided in the cap 274 of housing 290, thereby locking the handle to the remainder of the extraction tool 200. With the handle locked to the extractor tool, the user may then turn the handle thereby providing a rotational force to overcome any friction or other forces that might otherwise prevent successful extraction of the implant. The user may then, while holding the handle 237 with one hand, use a hammer or mallet with the other hand to strike the distal side of the strike plate 292 to generate extraction force sufficient to remove the implant from the bone in which it is embedded.

According to the exemplary embodiments of the subject disclosure, there is provided an implant extractor tool that can be operated by one hand, thereby rendering it easier to attach to an implant than currently available extractors that require two-handed operation. More specifically, the exemplary implant extractor tools enable the tools to quickly engage an implant to be extracted by a single press of a button, much like a trigger. In contrast, existing extractors require a user to hold the tool with one hand while turning an adjuster with the other hand until the jaws of the tool engage the implant. Such a procedure occupies both of the user's hands and requires considerable manual dexterity to align and hold the tool in the proper position with respect to the implant while turning the adjuster.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

We claim:

1. An implant extractor tool comprising:
a first arm having a proximal end for attachment to an extractor, and a distal end opposite the proximal end;
a second arm pivotably connected to the first arm, the second arm having a proximal end and a distal end;
an adjuster connected to one of the first and second arms for engaging abutting the other of the first and second arms;
a biasing member biasing one of the first and second arms; and
an actuator operatively engageable with the adjuster, wherein the actuator is movable between a first position locking the adjuster in a fixed position and a second position spaced from the adjuster permitting movement of the adjuster relative to the actuator.

2. The implant extractor tool of claim 1, wherein the adjuster comprises a threaded shaft and a control knob.

3. The implant extractor tool of claim 2, wherein the adjuster further comprises domed distal end.

4. The implant extractor tool of claim 1, wherein the biasing member surrounds the adjuster.

5. The implant extractor tool of claim 1, wherein the actuator comprises a latch moveable between a locking position for locking the adjuster in the fixed position and an unlocking position spaced from the adjuster.

6. The implant extractor tool of claim 5, wherein the latch is completely housed within one of the first and second arms.

7. The implant extractor tool of claim 1, wherein the actuator further comprises:
  a knob;
  a shaft extending from the knob;
  a latch about a distal end of the shaft; and
  an actuator biasing member biasing the latch.

8. The implant extractor tool of claim 1, wherein the adjuster is received within a through hole of one of the first and second arms.

9. The implant extractor tool of claim 1, further comprising a fastener configured to releasably attach an extractor to a proximal end of one of the first and second arms.

10. The implant extractor tool of claim 9, wherein the fastener comprises:
  a retaining housing having a central cavity for receiving a handle extension of an extractor; and
  a lock moveable between first and second positions relative to the retaining housing, the lock having a through hole for receiving the handle extension.

11. The implant extractor tool of claim 10, wherein the fastener further comprises a biasing member that biases the lock towards the first position.

12. The implant extractor tool of claim 11, wherein the lock defines a lip that partially occludes the central cavity from receiving the handle extension.

13. The implant extractor tool of claim 1, wherein at least one of the first and second arms comprises a latch for releasably retaining a respective first jaw or second jaw.

14. The implant extractor tool of claim 1, wherein the adjuster comprises a splined shaft and a bulbous end.

15. The implant extractor tool of claim 14, wherein the biasing member surrounds the splined shaft.

16. The implant extractor tool of claim 1, wherein the actuator further comprises:
  an actuation button;
  a shaft extending from the actuation button;
  a latch about a distal end of the shaft; and
  an actuator biasing member biasing the latch.

17. The implant extractor tool of claim 1, wherein the adjuster extends through a through hole of the actuator.

18. The implant extractor tool of claim 1, wherein the adjuster is housed completely within one of the first and second arms.

19. The implant extractor tool of claim 1, further comprising an arms biasing member biasing the first and second arms.

20. The implant extractor tool of claim 1, wherein one of the first and second arms includes a cam surface engaged with the adjuster.

21. The implant extractor tool of claim 1, wherein one of the first and second arms includes a fastener for releasably attaching an extractor or handle to its proximal end.

22. The implant extractor tool of claim 1, further comprising a handle attached to a proximal end of the first arm, and wherein the adjuster and actuator is mounted to the first arm.

23. The implant extractor tool of claim 1, further comprising a first jaw releasably attachable to the distal end of the first arm and a second jaw releasably attachable to the distal end of the second arm.

* * * * *